US007282201B2

(12) United States Patent
Miura et al.

(10) Patent No.: US 7,282,201 B2
(45) Date of Patent: Oct. 16, 2007

(54) METHODS OF PROMOTING THE GROWTH OR DIFFERENTIATION OF HEMATOPOIETIC STEM OR PROGENITOR CELLS BY NON-MUSCLE TYPE COFILIN

(75) Inventors: Kenju Miura, Osaka (JP); Munetada Haruyama, Hyogo (JP); Shiho Kodama, Osaka (JP)

(73) Assignee: Asubio Pharma Co., Ltd. (JP)

( * ) Notice: Subject to any disclaimer, the term of this patent is extended or adjusted under 35 U.S.C. 154(b) by 12 days.

(21) Appl. No.: 10/649,952

(22) Filed: Aug. 28, 2003

(65) Prior Publication Data

US 2004/0157326 A1    Aug. 12, 2004

Related U.S. Application Data

(63) Continuation of application No. PCT/JP02/13862, filed on Dec. 27, 2002.

(30) Foreign Application Priority Data

Dec. 28, 2001    (JP)    ............................. 2001-400330

(51) Int. Cl.
*A61K 35/14*    (2006.01)
*A61K 38/18*    (2006.01)
*A61K 38/19*    (2006.01)
*C07K 14/435*    (2006.01)
*C07K 14/475*    (2006.01)
*C07K 14/52*    (2006.01)
*C12N 5/00*    (2006.01)

(52) U.S. Cl. .................. 424/93.7; 424/198.1; 424/577; 435/4; 435/325; 435/375; 435/377; 530/350; 530/351; 530/399; 514/2; 514/12

(58) Field of Classification Search ................ 530/300, 530/350, 351, 399; 435/4, 7.1; 424/85.1, 424/184.1, 198.1; 514/2, 12
See application file for complete search history.

(56) References Cited

U.S. PATENT DOCUMENTS 5,464,817 A    11/1995    Stossel et al.

FOREIGN PATENT DOCUMENTS

| EP | 1 033 401 A2 | 9/2000 |
|---|---|---|
| JP | 05050603 | 3/1993 |
| JP | 06269284 A | 9/1994 |
| JP | 10067662 A | 3/1998 |
| JP | 10087484 A | 4/1998 |
| WO | WO94/22465 | 10/1997 |
| WO | WO 02/053719 A2 | 7/2002 |
| WO | WO-2004035092 A2 * | 4/2004 |

OTHER PUBLICATIONS

Vartiainen et al. The three mouse actin-depolymerizing factor/cofilins evolved to fulfill cell-type-specific requirements for actin dynamics. Mol Biol Cell. 13(1):183-194, 2002.*

Konakahara et al. CD29 integrin- and LIMK1/cofilin-mediated actin reorganization regulates the migration of haematopoietic progenitor cells underneath bone marrow stromal cells. Genes Cells. 9(4):345-358, 2004.*

Silva et al. The profile of gene expression of human marrow mesenchymal stem cells. Stem Cells. 21(6):661-669, 2003.*

Nagaoka et al. Effects of cofilin on actin filamentous structures in cultured muscle cells. Intracellular regulation of cofilin action. J Cell Sci. 108 (Pt 2):581-593, 1995.*

Aizawa et al. Cofilin-2, a novel type of cofilin, is expressed specifically at aggregation stage of Dictyostelium discoideum development. Genes Cells. 6(10):913-921, 2001.*

Herzer and Englert. "Nucleic Acid Hybridization". 2001. Molecular Biology Problem Solver: A Laboratory Guide. New York: Wiley-Liss, Inc, pp. 399-401, 424-425, 448-452.*

Pettit et al. The development of site-specific drug-delivery systems for protein and peptide biopharmaceuticals. Trends Biotechnol 16: 343-349, 1998.*

Svilvassy, S. The Biology of Hematopoietic Stem Cells. Arch Med Res 34: 446-460, 2003.*

Gillett, G.T. et al., "Mapping of human non-muscle type confilin (CFL1) to chromosome 11q13 and muscle-type cofilin (CFL2) to chromosome 14", Ann. Hum. Genet. (1996), vol. 60, pp. 201-211.

Götze, Katharina S. et al., "gp130-Stimultating designer cytokine Hyper-interleukin-6 synergizes with murine stroma for long-term survival of primitive human hematopoietic progenitor cells", Experimental Hematology 29 (2001), pp. 822-832.

Huang, Eric et al., "The Hematopoietic Growth Factor KL is Encoded by the SI Locus and is the Ligand of the c-kit Receptor, the Gene Product of the W Locus", Cell (Oct. 5, 1990), vol. 63, pp. 225-233.

Kawashima, Ichiro et al., "CD34+Human Marrow Cells That Express Low Levels of Kit Protein Are Enriched For Long-Term Marrow-Engrafting Cells", Blood (May 15, 1996), vol. 87, No. 10, pp. 4136-4142.

Kimura, Takafumi et al., "Simultaneous Activation of Signals Through gp130, c-kit, and Interleukin-3 Receptor Promotes a Trilineage Blood Cell Production in the Absence of Terminally Acting Lineage-Specific Factors", Blood (Dec. 15, 1997), vol. 90, No. 12, pp. 4767-4778.

Lyman PhD, Stewart D., "Biological effects and potential clinical applications of Flt3 ligand", Curr. Hematol. (1998), vol. 5, No. 3, pp. 192-196.

(Continued)

*Primary Examiner*—Bridget Bunner
(74) *Attorney, Agent, or Firm*—Hunton & Williams LLP

(57)    ABSTRACT

This invention has as its object providing promoters of the growth and/or differentiation of hematopoietic stem cells and/or hematopoietic progenitors which are useful as therapeutics of diseases that result from insufficient growth and/or differentiation of hematopoietic stem cells and/or hematopoietic progenitors, in particular, as therapeutics of panhematopenia and/or diseases that are accompanied by hematopoietic hypofunction. The invention attains the stated object by providing promoters of the growth and/or differentiation of hematopoietic stem cells and/or hematopoietic progenitors that contain Cofilin as an active ingredient.

19 Claims, 10 Drawing Sheets

OTHER PUBLICATIONS

Moon, Anne et al., "The ADF/Cofilin Proteins: Stimulus-responsive Modulators of Actin Dynamics", Molecular Biology of the Cell (Nov. 1995), vol. 6, pp. 1423-1431.

Moore, Malcolm A. S., "Clinical Implications of Positive and Negative Hematopoietic Stem Cell Regulators", Blood (Jul. 1, 1991), vol. 78, No. 1, pp. 1-19, The Journal of The American Society of Hematology.

Nakahata, Tatsutoshi et al., "Role of glycoprotein 130 and c-Kit signaling in proliferation and differentiation of human hematopoietic progenitor cells", Cancer Chemother Pharmacol (1996), vol. 38, (Suppl), pp. S64-S68.

Ogawa, K. et al., Coding sequence of human placenta Cofilin cDNA, Nucleic Acids Research (1990), vol. 18, No. 23.

Ogawa, Makio, "Differentiation and Proliferation of Hematopoietic Stem Cells", Blood (Jun. 1, 1993), vol. 81, No. 11, pp. 2844-2853.

Piacibello, Wanda et al., "Extensive Amplification and Self-Renewal of Human Primitive Hematopoietic Stem Cells From Cord Blood," Blood (Apr. 15, 1997), vol. 89, No. 8, pp. 2644-2653, Rapid Communication.

Williams, Douglas E. et al., "Identification of a Ligand for the c-kit Proto-Oncogene," Cell (Oct. 5, 1990), vol. 63, pp. 167-174.

Zsebo, Krisztina M. et al., "Identification, Purification, and Biological Characterization of Hematopoietic Stem Cell Factor from Buffalo Rat Liver-Conditioned Medium", Cell (Oct. 5, 1990), vol. 63, pp. 195-201.

MacIver et al. "The ADF/cofilin family: actin-remodeling proteins." Genome Biology, vol. 3, No. 5, 1-12 (2002).

Maekawa et al. (1984) "Isolation of Low Molecular Weight Actin-Binding Proteins from Porcine Brains." J. Biochem. 95: 377-385.

McGough et al. (Aug. 25, 1997) "Cofilin Changes the Twist of F-Actin: Implications for Actin Filament Dynamics and Cellular Function." The Journal of Cell Biology 138(4):771-781.

Nishida et al. (1984) "Cofilin, a Protein in Porcine Brain that binds to Actin Filaments and Inhibits their Interactions with Myosin and Tropomyosin." Biochemistry 23: 5307-5313.

* cited by examiner

Primary structure of human nonmuscle-type cofilin
(AC: P23528)

M<u>ASGVAVSDG VIKVFNDMKV</u> RKSSTPEEVK KRKKAVLFCL SEDKKNIILE
EGKEILVGDV
GQTVDDPYAT FVKMLPDKDC R<u>YALYDATYE TK</u>ESKKEDLV FIFWAPESAP
LKSKMIYASS
KDAIKKKLTG IKHELQANCY EEVKDRCTLA EK<u>LGGSAVIS LEGKPL</u>

The underlined portions are the sites analyzed for sequence by MS and MS/MS.

Met <u>Ala Ser Gly Val Ala Val Ser Asp Gly Val Ile Lys</u> Val Phe Asn
           5          10          15

Asp Met Lys Val Arg Lys Ser Ser Thr Pro Glu Glu Val Lys Lys Arg
         20          25         30

Lys Lys Ala Val Leu Phe Cys Leu Ser Glu Asp Lys Lys Asn Ile Ile
         35          40         45

Leu Glu Glu Gly Lys Glu Ile Leu Val Gly Asp Val Gly Gln Thr Val
         50          55         60

Asp Asp Pro Tyr Ala Thr Phe Val Lys Met Leu Pro Asp Lys Asp Cys
         65          70         75         80

Arg <u>Tyr Ala Leu Tyr Asp Ala Thr Tyr Glu Thr Lys</u> Glu Ser Lys Lys
         85          90         95

Glu Asp Leu Val Phe Ile Phe Trp Ala Pro Glu Ser Ala Pro Leu Lys
         100         105         110

Ser Lys Met Ile Tyr Ala Ser Ser Lys Asp Ala Ile Lys Lys Lys Leu
         115         120         125

Thr Gly Ile Lys His Glu Leu Gln Ala Asn Cys Tyr Glu Glu Val Lys
         130         135         140

Asp Arg Cys Thr Leu Ala Glu Lys <u>Leu Gly Gly Ser Ala Val Ile Ser</u>
145               150         155         160

<u>Leu Glu Gly Lys Pro Leu</u>    SEQ ID NO: 1
        165

Fig. 1 cDNA of human placental nonmuscle-type cofilin
(AC: D00682)

<u>atggcctccg gtgtggctgt ctctgatggt</u> gtcatcaagg tgttcaacga catgaaggtg  60
cgtaagtctt caacgccaga ggaggtgaag aagcgcaaga aggcggtgct cttctgcctg 120
agtgaggaca agaagaacat catcctggag gagggcaagg agatcctggt gggcgatgtg 180
ggccagactg tcgacgatcc ctacgccacc tttgtcaaga tgctgccaga taaggactgc 240
cgctatgccc tctatgatgc aacctatgag accaaggaga gcaagaagga ggatctggtg 300
tttatcttct gggcccccga gtctgcgccc cttaagagca aaatgattta tgccagctcc 360
aaggacgcca tcaagaagaa gctgacaggg atcaagcatg aattgcaagc aaactgctac 420
gaggaggtca aggaccgctg caccctggca gagaagctgg ggggcagtgc ggtca<u>tctcc</u> 480

<u>ctggagggca agcctttgtg a</u>   SEQ ID NO: 2                    501

The underlined portions are the sites where two oligomers were synthesized as primers.

Fig. 2

Alignment of the base sequences for nonmuscle-type cofilin
derived from human placenta (upper)
and from human S6 cells (lower).

```
                        10         20         30         40         50
Placental cDNA     1 ATGGCCTCCG GTGTGGCTGT CTCTGATGGT GTCATCAAGG
TGTTCAACGA   50
S6 cDNA            1 ATGGCCTCCG GTGTGGCTGT CTCTGATGGT GTCATCAAGG
TGTTCAACGA   50

60         70         80         90        100
Placental cDNA    51 CATGAAGGTG CGTAAGTCTT CAACGCCAGA GGAGGTGAAG
AAGCGCAAGA  100
S6 cDNA           51 CATGAAGGTG CGTAAGTCTT CAACGCCAGA
GGAGGTGAAG AAGCGCAAGA  100

110        120        130        140        150
Placental cDNA   101 AGGCGGTGCT CTTCTGCCTG AGTGAGGACA AGAAGAACAT
CATCCTGGAG  150
S6 cDNA          101 AGGCGGTGCT CTTCTGCCTG AGTGAGGACA
AGAAGAACAT CATCCTGGAG  150

160        170        180        190        200
Placental cDNA   151 GAGGGCAAGG AGATCCTGGT GGGCGATGTG GGCCAGACTG
TCGACGA$CC   200
S6 cDNA          151 GAGGGCAAGG AGATCCTGGT GGGCGATGTG
GGCCAGACTG TCGACGA$CC   200

210        220        230        240        250
Placental cDNA   201 CTACGCCACC TTTGTCAAGA TGCTGCCAGA TAAGGACTGC
CGCTATGCCC  250
S6 cDNA          201 CTACGCCACC TTTGTCAAGA TGCTGCCAGA TAAGGACTGC
CGCTATGCCC  250

260        270        280        290        300
Placental cDNA   251 TCTATGATGC AACCTATGAG ACCAAGGAGA GCAAGAAGGA
GGATCTGGTG  300
S6 cDNA          251 TCTATGATGC AACCTATGAG ACCAAGGAGA
GCAAGAAGGA GGATCTGGTG  300

310        320        330        340        350
Placental cDNA   301 TTTATCTTCT GGGCCCCCGA GTCTGCGCCC CTTAAGAGCA
AAATGATTTA  350
S6 cDNA          301 TTTATCTTCT GGGCCCCCGA GTCTGCGCCC CTTAAGAGCA
AAATGATTTA  350

360        370        380        390        400
Placental cDNA   351 TGCCAGCTCC AAGGACGCCA TCAAGAAGAA GCTGACAGGG
ATCAAGCATG  400
S6 cDNA          351 TGCCAGCTCC AAGGACGCCA TCAAGAAGAA
GCTGACAGGG ATCAAGCATG  400

410        420        430        440        450
Placental cDNA   401 AATTGCAAGC AAACTGCTAC GAGGAGGTCA AGGACCGCTG
CACCCTGGCA  450
S6 cDNA          401 AATTGCAAGC AAACTGCTAC GAGGAGGTCA
AGGACCGCTG CACCCTGGCA  450

460        470        480        490        500
Placental cDNA   451 GAGAAGCTGG GGGGCAGTGC $GTCATCTCC CTGGAGGGCA
AGCCTTTGTG  500
S6 cDNA          451 GAGAAGCTGG GGGGCAGTGC $GTCATCTCC
CTGGAGGGCA AGCCTTTGTG  500

510        520        530        540        550
Placental cDNA   501 A.................................. 550    SEQ ID NO: 2
S6 cDNA              501 A............................ 550    SEQ ID NO: 8
```
The two bases that differ between the two sequences are marked
by shadowing and are both due to silent mutation.

Fig. 3

A
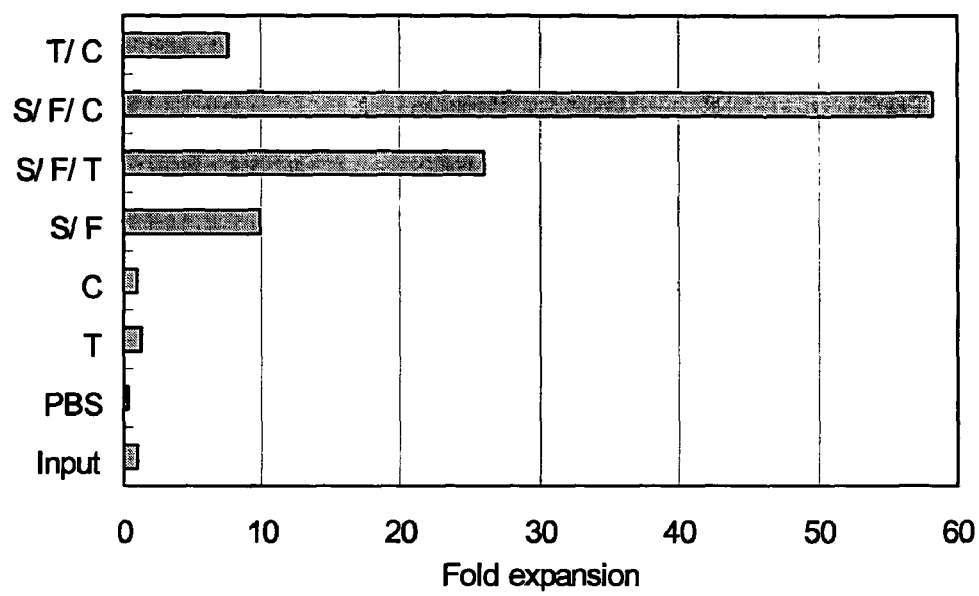
B
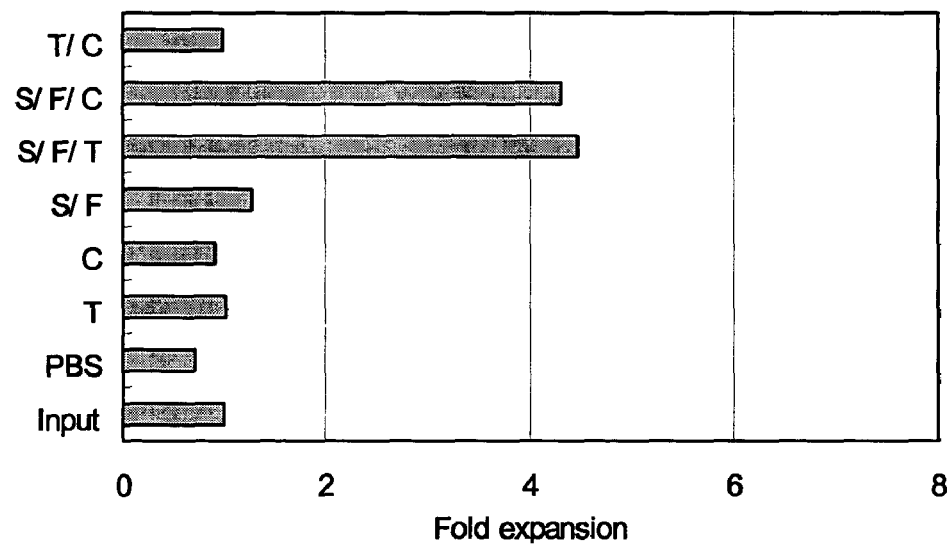
Fig. 6

C
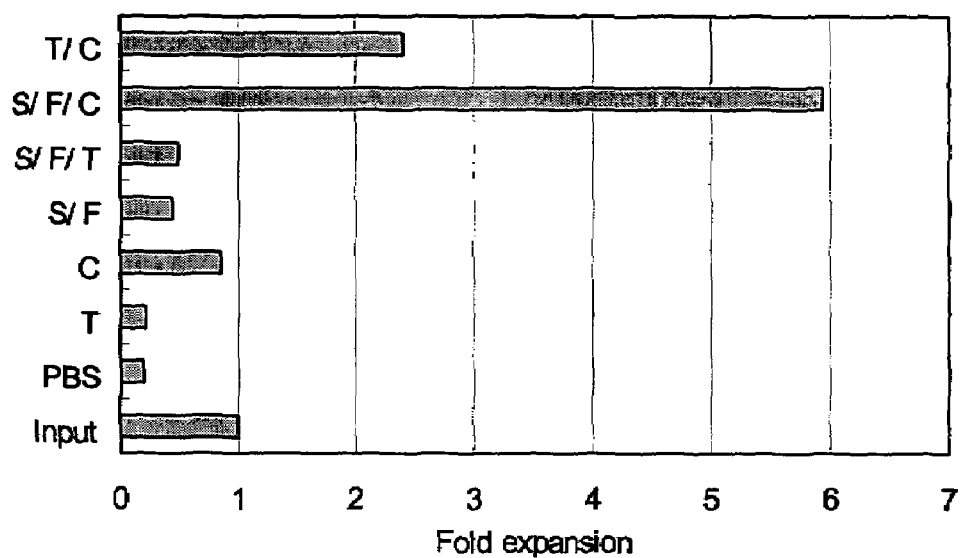
D
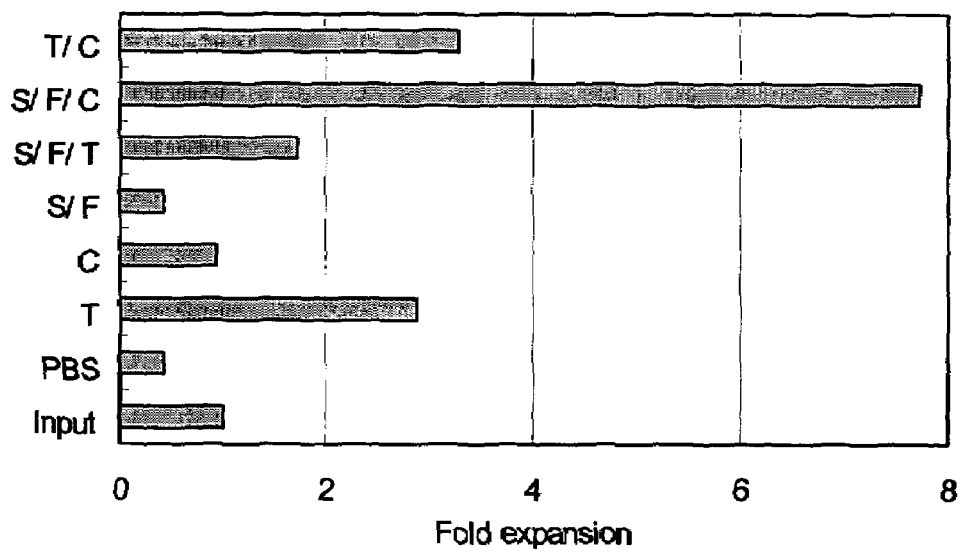
Fig. 6 (Cont.)

SEQUENCE LISTING

<160> NUMBER OF SEQ ID NOS: 4

<210> SEQ ID NO 1
<211> LENGTH: 166
<212> TYPE: PRT

```
<213> ORGANISM: Human

<400> SEQUENCE: 1

Met Ala Ser Gly Val Ala Val Ser Asp Gly Val Ile Lys Val Phe Asn
                 5                  10                  15

Asp Met Lys Val Arg Lys Ser Ser Thr Pro Glu Glu Val Lys Lys Arg
             20                  25                  30

Lys Lys Ala Val Leu Phe Cys Leu Ser Glu Asp Lys Lys Asn Ile Ile
         35                  40                  45

Leu Glu Glu Gly Lys Glu Ile Leu Val Gly Asp Val Gly Gln Thr Val
     50                  55                  60

Asp Asp Pro Tyr Ala Thr Phe Val Lys Met Leu Pro Asp Lys Asp Cys
 65                  70                  75                  80

Arg Tyr Ala Leu Tyr Asp Ala Thr Tyr Glu Thr Lys Glu Ser Lys Lys
                 85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
        115                 120                 125

Thr Gly Ile Lys His Glu Leu Gln Ala Asn Cys Tyr Glu Glu Val Lys
    130                 135                 140

Asp Arg Cys Thr Leu Ala Glu Lys Leu Gly Gly Ser Ala Val Ile Ser
145                 150                 155                 160

Leu Glu Gly Lys Pro Leu
                165

<210> SEQ ID NO 2
<211> LENGTH: 501
<212> TYPE: DNA
<213> ORGANISM: Human

<400> SEQUENCE: 2
atggcctccg gtgtggctgt ctctgatggt gtcatcaagg tgttcaacga catgaaggtg      60
cgtaagtctt caacgccaga ggaggtgaag aagcgcaaga aggcggtgct cttctgcctg     120
agtgaggaca agaagaacat catcctggag gagggcaagg agatcctggt gggcgatgtg     180
ggccagactg tcgacgatcc ctacgccacc tttgtcaaga tgctgccaga taaggactgc     240
cgctatgccc tctatgatgc aacctatgag accaaggaga gcaagaagga ggatctggtg     300
tttatcttct gggccccccga gtctgcgccc cttaagagca aaatgattta tgccagctcc     360
aaggacgcca tcaagaagaa gctgacaggg atcaagcatg aattgcaagc aaactgctac     420
gaggaggtca aggaccgctg caccctggca gagaagctgg ggggcagtgc ggtcatctcc     480
ctggagggca agcctttgtg a                                                501

<210> SEQ ID NO 3
<211> LENGTH: 26
<212> TYPE: DNA
<213> ORGANISM: Artificial Sequence
<220> FEATURE:
<223> OTHER INFORMATION: Primer sequence for amplifying human
      Cofilin gene

<400> SEQUENCE: 3
atggcctccg gtgtggctgt ctctga                                           26

<210> SEQ ID NO 4
<211> LENGTH: 26
```

-continued

```
<212> TYPE: DNA
<213> ORGANISM: Artificial Sequence
<220> FEATURE:
<223> OTHER INFORMATION: Primer sequence for amplifying human
      Cofilin gene

<400> SEQUENCE: 4
tctccctgga gggcaagcct ttgtga                                          26
```

METHODS OF PROMOTING THE GROWTH OR DIFFERENTIATION OF HEMATOPOIETIC STEM OR PROGENITOR CELLS BY NON-MUSCLE TYPE COFILIN

This application is a continuation of PCT/JP02/13862, filed on Dec. 27, 2002, which claims benefit of priority of Japanese Patent Application No. 400330/2001, filed Dec. 28, 2001.

FIELD OF INVENTION

This invention relates to promoters of the growth and/or differentiation of hematopoietic stem cells and/or hematopoietic progenitors that contain Cofilin as an active ingredient which constitute a class of actin binding proteins or analogous compounds of Cofilin, as well as new uses of the promoters. The present promoters of the growth and/or differentiation of hematopoietic stem cells and/or hematopoietic progenitors are useful as therapeutics of diseases that result from insufficient growth and/or differentiation of hematopoietic stem cells and/or hematopoietic progenitors, in particular, as therapeutics of panhematopenia and/or diseases that are accompanied by hematopoietic hypofunction. The present promoters of the growth and/or differentiation of hematopoietic stem cells and/or hematopoietic progenitors may be used to expannd hematopoietic stem cells ex vivo and this method is useful in transplantation of hematopoietic stem cells and in gene therapy and even in regenerative medicine.

BACKGROUND OF INVENTION

Hematopoiesis is regulated by the direct interaction between the group of hematopoietic stem cells having self-renewing capacity, hematopoietic progenitors supplied from hematopoietic stem cells and destined to differentiate in a predetermined direction and cells at various stages of continuous differentiation from the former to the latter, and supporting stroma cells as a hematopoietic micro-environment that surrounds those sets of cells, or by the indirect interaction between the first mentioned group of cells and humoral hematopoietic regulating factors secreted from the stroma cells. A large number of cytokines have been shown to participate in the growth and/or differentiation of hematopoietic stem cells into various mature blood cells via hematopoietic progenitors.

The development of genetic engineering has witnessed the gene cloning of the cytokines mentioned above and their industrial production has also become possible by genetic recombination technology. Among genetic recombinant hematopoietic factors are the granulocyte colony-stimulating factor (hereunder abbreviated as G-CSF) and the macrophage colony-stimulating factor (hereunder abbreviated as M-CSF) which are clinically applied as therapeutics of hematopoietic hypofunction (e.g. neutropenia) due to radiation exposure or chemotherapy, as well as erythropoietin (hereunder abbreviated as EPO) which is clinically applied as a therapeutic of renal anemia. However, the treatment with these hematopoietic factors simply leads to a temporary recovery of mature blood cells.

Hence, auto- or homo-grafting of hematopoietic stem cells has been performed as a means of treatment for fundamental improvement of hematopoietic function. Recently, peripheral hematopoietic stem cells transplantation has been spread rapidly and umbilical cord blood hematopoietic stem cells transplantation is drawing attention. However, they also involve many problems and, in particular, the rarity of hematopoietic stem cells in blood cells impose substantial burden on the donor and/or the recipient. It is therefore necessary to establish a method for ex vivo expansion of hematopoietic stem cells. Patients with lethal hereditary diseases, certain malignant tumors and AIDS, which currently have no effective methods of treatment, are being subjected to trials of gene therapy for complementing deficient or mutated genes (Juya Ohashi, Jikken Igaku, 12:333, 1994).

Hematopoietic stem cells, being capable of long time survival, are considered optimal target cells in gene therapy of the kind just described above. However, in order to achieve efficient transfection or infection with a retrovirus vector incorporating a desired gene, it is usually required that a small number of hematopoietic stem cells in the resting phase be put into the cell cycle and proliferated. Studies have been made on the effect of a stem cell factor (SCF) and flk-2/flt-3 ligand which are considered to participate in the growth of hematopoietic stem cells and hematopoietic progenitors.

It has been revealed by experimental studies that the c-kit/SCF signal is important for the growth of hematopoietic stem cells and hematopoietic progenitors (Blood, 78:1-19, 1991; Blood, 81: 2844-2853, 1993; Blood, 90:4767-4778, 1997) and the stem cell factor (SCF) has been shown to be a ligand for the c-kit which is the tyrosine kinase type receptor expressed in hematopoietic stem cells and hematopoietic progenitors (Cell, 63:167-174, 1990; Cell, 63:195-201, 1990; Cell, 63:225-233, 1990), leading researchers to anticipate that SCF may have effect on the growth of hematopoietic stem cells and hematopoietic progenitors. However, the c-kit is expressed only weakly on human hematopoietic stem cells and hematopoietic progenitors (Blood, 87:4136-4142, 1996) and SCF if used alone has low expansion activity and is not fully effective for the growth of hematopoietic stem cells and hematopoietic progenitors.

flk-2/flt-3 is a receptor type tyrosine kinase with recognized gene expression in various tissues and, in blood cells, is dominantly expressed in undifferentiated hematopoietic stem cells, with the flk-2/flt-3 ligand (FL) having been identified as a factor stimulating the growth of undifferentiated hematopoietic cells (Lyman, S. D. Curr. Opin. Hematol., 1998; 5(3): 192-6). But then this molecule, if used alone, has low expansion activity and is not fully effective for the growth of hematopoietic stem cells and hematopoietic progenitors.

Thus, neither SCF nor FL is fully effective for the growth of hematopoietic stem cells and hematopoietic progenitors if they are used singly, so combining them with various cytokines is considered ideal as a method of expansion hematopoietic stem cells and hematopoietic progenitors (Blood, 89: 2644-2653, 1997; Cancer Chemother. Pharmacol., 38[Suppl.]:64-68, 1996) and a study has been made on combining these molecules with TPO (thrombopoietin), interleukin 6 (IL-6)/soluble interleukin 6 receptor complex, Hyper IL-6 (fusion protein from IL-6 and IL-6 receptor), etc. (Exp. Hematol. 29:822-832, 2001). Further, it is desired to elucidate and obtain a new factor having stronger expansion activity.

Cofilin is a protein having molecular weight of about 19,000 and a member of actin-binding proteins (ABP) that bind to actin filaments (F-actin) at a molar ratio of 1:1 in response to a variety of signals, thus regulating the physical conditions of actin and performing primary function in the reconstitution of the actin-based cytoskeleton (Jikken Igaku, Vol. 12, No. 4:24-28, 1994). It is known that Cofilin, by binding to G-actin and cutting G-actin (actin monomer) and depolymerizing it, controls many cell responses including changes in shape, movements (motion), division, secretion, phagocytic (pinocytic) action, various signal transductions, etc. (Seikagaku, Vol. 71, No. 2:101-114, 1999). Cofilin in a cell occurs in both a phosphorylated and a dephosphorylated form and their activity for binding to actin is suppressed by phosphorylation but promoted by dephosphorylation.

It has recently become known that Cofilin is dephosphorylated in response to various external stimulations including the stimulation of platelets by thrombin, the stimulation of thyroid cells by a thyroid-stimulating hormone, the stimulation of parotid cells by isoproterenol and the stimulation of astrocytes by dibutyryl cAMP (Moon, A. & Drubin, D. G. (1995) Mol. Biol. Cell. 6, 1423-1431). It has also been reported that Cofilin is dephosphorylated as neutrophils or T cells are activated.

Methods have been proposed that are intended to treat certain kinds of disease either through the function of actin binding proteins (ABPs) or by regulating the ABP function. Included among such methods are those for treatment or disease alleviation by administering ABP to morbid tissues or organs resulting from actin deposits (JP 5-50603 A and JP 8-510998 A), as well as therapeutics for a variety of failure-to-control-apotosis associated diseases that act under the mechanism of apoptosis modulation by suppressors of dephosphorylation of Cofilin (JP 10-67662 A and JP 10-87484 A).

However, to date there has been no report of Cofilin and their analogous compounds participating in the growth and/or differentiation of hematopoietic stem cells and/or hematopoietic progenitors.

An object of the present invention is to provide promoters of the growth and/or differentiation of hematopoietic stem cells and/or hematopoietic progenitors that are useful as therapeutics of diseases that develop from insufficient growth and/or differentiation of hematopoietic stem cells and/or hematopoietic progenitors, in particular, panhematopenia and/or diseases that are accompanied by hematopoietic hypofunction. Another object of the present invention is to provide a method of expanding hematopoietic stem cells ex vivo which comprises administering the promoters of the growth and/or differentiation of hematopoietic stem cells and/or hematopoietic progenitors, which method is also useful in transplantation of hematopoietic stem cells, gene therapy and regenerative medicine.

SUMMARY OF THE INVENTION

The present inventors previously treated a human bone marrow leukemic cell line and established a new cell line characterized by positive expression of CD34 and negative expression of GP (glycoprotein) IIb/IIIa (JP 6-269284 A). The inventors designated the cell as human myeloid leukemic cell S6 SBM332 (which is hereunder referred to as S6 cell) and it was deposited as FERM BP-4227 with the National Institute of BioScience and Human-Technology, Agency of Industrial Science and Technology, Ministry of International Trade and Industry (now the International Patent Organism Depositary, National Institute of Advanced Industrial Science and Technology) at 1-1-1, Higashi, Tsukuba, Ibaragi, Japan under date of Mar. 9, 1993. CD34 is a glycoprotein that disappears as hematopoietic stem cells differentiate and is a marker of human hematopoietic stem cells, and GP (glycoprotein) IIb/IIIa is a platelet membrane glycoprotein that is expressed specifically in platelets and megakaryocytes and is a marker of human megakaryocytes which is a differentiated antigen that is potentiated as megakaryocytes differentiate.

The S6 cell line is capable of consistent long-term culture in the presence of serum while retaining the positive expression of CD34 and the negative expression of GP IIb/IIIa and, what is more, as the result of culture in the presence of 12-O-tetradecanoyl phorbol 13-acetate (PTA), the expression of CD34 is attenuated whereas that of GP IIb/IIIa is considerably enhanced. Thus, it has been found that the S6 cell line differentiates to a megakaryocyte lineage, evidently having the capability of differentiation.

The inventors of the present invention made further studies on the basis of those conventional experimental results and found that the serum-free culture supernatant of S6 cells contained a factor that promoted the expansion of mouse high proliferative potential-colony forming cells (HPP-CFCs). From the heretofore obtained findings and the results of their studies, the present inventors found that S6 cells had the nature of hematopoietic stem cells and were undergoing autocrine growth in the presence of an unknown factor (hereunder referred to as S6 factor) capable of promoting the growth of hematopoietic stem cells. Thus, there was suggested a possibility that the S6 factor is a novel growth factor for hematopoietic stem cells and/or hematopoietic progenitors. On the basis of this possibility, the inventors purified the protein-free culture supernatant of S6 cells and made intensive studies covering not only the separation and purification of the factor having the HPP-CFC expansion capacity, as well as determination of its structure or cloning of the gene of that factor, but also the HPP-CFC expansion capacity of a genetic recombined factor. Unexpectedly enough, it was found that the factor of interest was Cofilin, low-molecular weight actin binding proteins.

This finding led the inventors of the present invention to discover that Cofilin constituting a member of actin binding proteins was a factor capable of promoting the growth and/or differentiation of hematopoietic stem cells and/or hematopoietic progenitors and the inventors were brought to accomplish the present invention on the basis of the finding that Cofilin could promote the HPP-CFC expansion in mice, exhibiting a remarkably higher activity than existing cytokines having the HPP-CFC expansion capacity.

Thus, the present invention provides promoters for the growth and/or differentiation of hematopoietic stem cells and/or hematopoietic progenitors which contain Cofilin as an active ingredient and which may further contain another cytokine as an optional component.

The present invention also provides a method of promoting the growth and/or differentiation of hematopoietic stem cells and/or hematopoietic progenitors which comprises administering at least one of the above-mentioned promoters for the growth and/or differentiation of hematopoietic stem cells and/or hematopoietic progenitors.

The present invention also provides a method of treating diseases that result from insufficient growth and/or differentiation of hematopoietic stem cells and/or hematopoietic progenitors, more specifically, panhematopenia and/or hematopoietic hypofunction by using at least one of the promoters for the growth and/or differentiation of hematopoietic stem cells and/or hematopoietic progenitors.

The present invention further provides a method of expanding hematopoietic stem cells ex vivo which comprises administering at least one of the above-mentioned promoters for the growth and/or differentiation of hematopoietic stem cells and/or hematopoietic progenitors.

The present invention still further provides a method of regenerative medicine comprising the steps of expanding hematopoietic stem cells ex vivo using at least one of the promoters for the growth and/or differentiation of hematopoietic stem cells and/or hematopoietic progenitors and transplanting the expanded hematopoietic stem cells.

This invention provides promoters of the growth and/or differentiation of hematopoietic stem cells and/or hematopoietic progenitors that contain Cofilin as an active ingredient and by so doing, it offers the advantage of being able to promote the growth and/or differentiation of a wide set of blood cells. By virtue of this advantage, the promoters are useful as therapeutics of panhematopenia and/or diseases that are accompanied by hematopoietic hypofunction. Further, the promoters enable efficient regeneration of blood associated cells in the field of regenerative medicine.

BRIEF DESCRIPTION OF THE DRAWINGS

FIG. 1 is a diagram showing the sequence for the primary structure of human nonmuscle-type Cofilin (AC: P23528).

FIG. 2 is a diagram showing the sequence of cDNA in human placental nonmuscle-type Cofilin (AC: D00682), with the underlined portions being the sites where two oligomers were synthesized as primers, i.e., primer SK013 (SEQ ID NO:3) and primer SK014 (SEQ ID NO:4).

FIG. 3 shows the alignment of the base sequences for nonmuscle-type Cofilin derived from human placenta (upper) and nonmuscle-type Cofilin derived from human S6 cells (lower), provided that the differences at base numbers 198 and 471 are both due to silent mutation.

FIG. 6A shows that human nonmuscle-type Cofilin as combined with SCF+FL caused a marked expansion of human umbilical cord blood derived CD34 positive cells.

FIGS. 6B-6D show that when human umbilical cord blood derived CD34 positive cells as grown under the condition of human nonmuscle-type Cofilin+SCF+FL were subjected to colony forming assay, significant increases occurred in the colony numbers of CFU-GM, BFU-E and CFU-Mix, respectively.

DETAILED DESCRIPTION OF PREFERRED EMBODIMENTS

Figure 4:
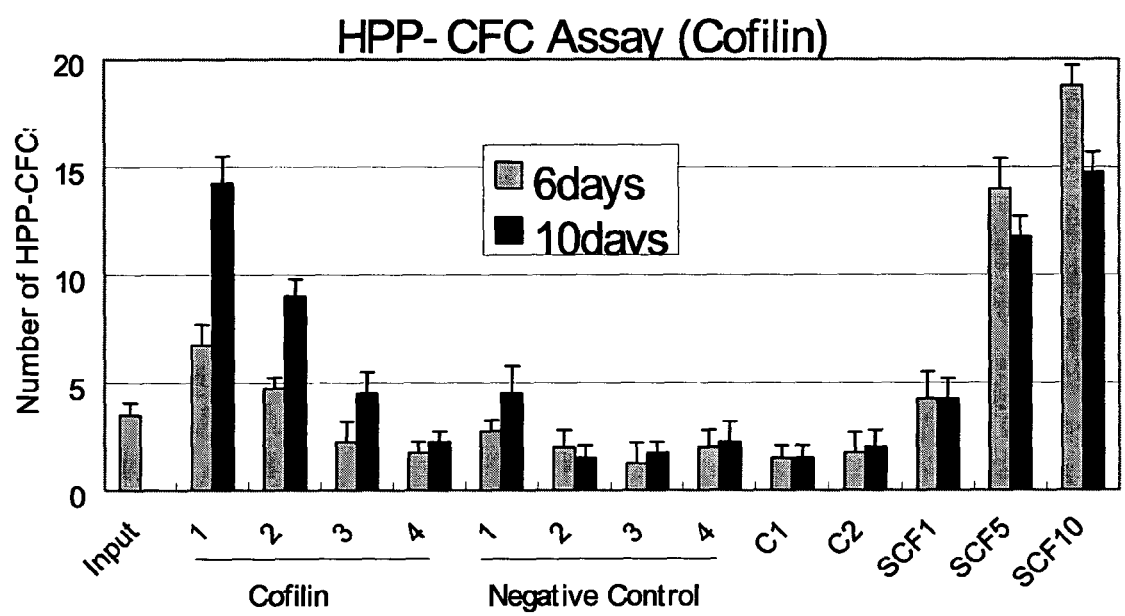
FIG. 4 shows the result of HPP-CFC assay on the hematopoietic stem cell expanding action of a culture supernatant of COS-1 cells in which recombinant human nonmuscle-type Cofilin had been expressed.

The activity of the Cofilin of the present invention in promoting the growth and/or differentiation of hematopoietic stem cells and/or hematopoietic progenitors can be determined by treating these cells with the Cofilin under the culture conditions and screening the growth and/or differentiation of these cells.

The activity of the Cofilin of the present invention in promoting the growth and/or differentiation of hematopoietic stem cells and/or hematopoietic progenitors can be determined with reference to the activity in promoting the expansion of HPP-CFCs (hereunder referred to as HPP-CFC activity). HPP-CFC stands for high proliferative potential-colony forming cells which are the most immature cells among those cells that can be verified by in vitro colony forming assay to have strong enough expanding power to form macroscopic colonies; they are considered to have differentiated one stage further than long term culture-initiating cells (LTC-ICs) which are detected as cells that retain the colony forming capacity even after culturing bone marrow cells on stroma cells for at least 5 weeks. The term HPP-CFC activity as used in the present invention means the activity of a substance under test in acting on HPP-CFCs to promote their expansion.

The HPP-CFC activity may be determined by the following procedure: with a view to obtaining hematopoietic stem cells specifically, T cells, B cells, granulocytes and macrophages were removed from anti-cancer agent 5-fluorouracil treated murine bone marrow cells to prepare hematopoietic stem cell fractions; after adding a sample and/or cytokines, the hematopoietic stem cell fractions are subjected to liquid culture and part of the conditioned medium including the hematopoietic stem cells is subjected to colony assay; the number of the resulting macroscopic HPP-CFC colonies is counted. By means of this procedure one can determine the activity of the promoter of the invention for the growth and/or differentiation of hematopoietic stem cells and/or hematopoietic progenitors.

When Cofilin was used in the present invention to determine the above-described HPP-CFC activity, they were found to act on HPP-CFCs and exhibit the activity of inducing their growth and/or differentiation. Therefore, Cofilin acts on multipotent stem cells, or those hematopoietic stem cells and/or hematopoietic progenitors which are at the very early stage of the process of their growth and/or differentiation, thereby promoting the growth and/or differentiation of such multipotent stem cells.

The term "hematopoietic stem cells" as used in the invention means multipotent stem cells that are capable of differentiating into all blood cells including erythrocytes, leukocytes and platelets. These are cells that are CD34 positive but negative for all other lineage markers. For instance, the "hematopoietic stem cells" as used in the invention are contained not only in bone marrow derived CD34 positive cells but also in umbilical cord blood derived CD34 positive cells.

The term "hematopoietic progenitors" as used in the present invention means those progenitors which are differentiated further than hematopoietic stem cells but are yet to differentiate into progenitors of respective blood cell lineages (unipotent precursor cells). For example, the "hematopoietic progenitors" as used in the present invention include granulocyte/mactophage associated progenitors (colony-forming unit granuloyte, macrophage, CFU-GM), erythroid associated progenitors (burst-forming unit erythroid, BFU- E), megakaryocyte associated progenitors (colony-forming unit megakaryocyte, CFU-Mk), and myeloid associated stem cells (colony-forming unit mixed, CFU-Mix).

The term "differentiation" of hematopoietic stem cells and/or hematopoietic progenitors as used in the invention means both the change of hematopoietic stem cells into hematopoietic progenitors and the change of hematopoietic progenitors into unipotent hematopoietic progenitors and/or cells having characteristic functions, namely mature cells including erythrocytes, leukocytes and megakaryocytes.

Consequently, the activity of promoting the growth of hematopoietic stem cells and/or hematopoietic progenitors as used in the invention means the activity by which hematopoietic stem cells and/or hematopoietic progenitors having the above-described functions are expanded to proliferate those hematopoietic stem cells and/or hematopoietic progenitors which have the same functions. Further, the activity of promoting the differentiation of hematopoietic stem cells and/or hematopoietic progenitors as used in the invention means the activity by which hematopoietic stem cells and/or hematopoietic progenitors are differentiated so that they are changed to those hematopoietic progenitors which have the above-described functions, myeloid associated stem cells, unipotent progenitors and/or mature blood cells (erythrocytes, leukocytes and megakaryocytes). In the present invention, the term HPP-CPC is used as a synonym for hematopoietic stem cells and/or hematopoietic progenitors.

Cofilin as an example of cleavage factors refers to a group of actin binding proteins of low molecular weights (15-21 kDa) that occur universally in eukaryotes and Cofilin in every higher vertebrate animal each consist of 166 amino acids. The amino acid sequences in those Cofilin has at least 30% full-length homology even between phylogenetically remote species. For example, human Cofilin occurs in both muscle-type and nonmuscle-type types and these are known to have 76.5% homology. Therefore, when the term "Cofilin" is used without any qualification in the present invention, it covers not only Cofilin having the amino acid sequence depicted by SEQ ID NO:1 but also its analogous compounds.

Analogous compounds of Cofilin as referred to in the invention include the following which all have the activity of promoting the growth and/or differentiation of hematopoietic stem cells and/or hematopoietic progenitors: one comprising the amino acid sequence of Cofilin depicted by SEQ ID NO:1 except that it has one or more amino acid deletions, substitutions and/or additions; one comprising an amino acid sequence encoded by a base sequence hybridizable under stringent conditions with a base sequence complementary to the base sequence coding for the amino acid sequence of Cofilin depicted by SEQ ID NO:1; and one comprising an amino acid sequence having at least 30%, preferably at least 50%, more preferably at least 60%, and most preferably at least 70%, amino acid sequence homology with the anmio acid sequence of Cofilin (SEQ ID NO:1). Analogous compounds of Cofilin as referred to in the invention also include the following which all have the activity of promoting the growth and/or differentiation of hematopoietic stem cells and/or hematopoietic progenitors: one encoded by a base sequence hybridizable under stringent conditions with a base sequence complementary to the base sequence coding for the base sequence of Cofilin depicted by SEQ ID NO:2; and one encoded by DNA comprising a base sequence having at least 30%, preferably at least 50%, more preferably at least 60%, and most preferably at least 70%, base sequence homology with the base sequence of Cofilin depicted by SEQ ID NO:2.

The words "one or more" preferably refer to 1-20, more preferably 1-10, and most preferably 1-5. In the case of proteins, "deletions", "substitutions" and "additions" refer to those which as in the case of Cofilin (SEQ ID NO:1) occur in such a way as to present the activity of promoting the growth and/or differentiation of hematopoietic stem cells and/or hematopoietic progenitors. Take, for example, the case of amino acid "substitutions"; they include replacements of one amino acid by another having a similar property, say, replacement of a certain hydrophobic amino acid by another hydrophobic amino acid, replacement of a certain hydrophilic amino acid by another hydrophilic ammo acid, replacement of a certain acidic amino acid by another acidic amino acid, and replacement of a certain basic amino acid by another basic ammo acid.

The stringent conditions as referred to in the present invention mean those conditions under which a desired base sequence is capable of specific hybridization with a base sequence (e.g. SEQ ID NO:2) that codes for Cofilin (SEQ ID NO:1) or a base sequence degenerate to it. Hybridizing conditions are determined in consideration of such factors as temperature and ion concentration and it is generally known that the higher the temperature and the lower the ion concentration, the higher the degree of stringency. Any person skilled in the art can set suitable stringent conditions on the basis of the descriptions in, for example, Sambrook and Russel (Molecular Cloning: A Laboratory Manual, 3rd edition (2001)). Such stringent conditions may specifically be exemplified by the use of hybridizing conditions such as 6×SSC, 5× Denhardt's, 0.1% SDS, 25° C.-68° C. A more preferred hybridization temperature may be 45° C.-68° C. (without formamide) or 25° C.-50° C. (with 50% formamide).

In the present invention, the amino acid or base sequence homology may be determined by a visual test and mathematical calculations. Alternatively, the homology between two protein sequences may be determined by comparing two sets of sequence information based on the algorithm of Needleman and Wunsch (J. Mol. Biol., 48:443-453, 1970) and using a GAP computer program available from the Wisconsin University Genetics Computer Group (UWGCG). Preferred default parameters in the GAP program include: (1) scoring matrix blosum62 as described in Henikoff and Henikoff (Proc. Natl. Acad. Sci. USA, 89:10915-10919, 1992); (2) 12 gap weights; (3) 4 gap length weights; and (4) no penalty for terminal gaps.

For analysis of amino acid or base sequence homology in the present invention, other programs used by skilled artisans for sequence comparison may also be employed. For example, homology determination can be made by comparing sequence information using the BLAST program described in Altschul et al. (Nucl. Acids Res. 25, p. 3389-3402, 1997). Specifically, in the case of base sequence analysis, Query base sequence may be entered on Nucleotide BLAST (BLASTN) program and checked against base sequence databases such as GenBank, EMBL and DDBJ. In the case of amino acid sequence analysis, Query amino acid sequence may be entered on Protein BLAST (BLASTP) program and checked against amino acid sequence databases such as GenBank CDS, PDB, SwissProt and PIR. The programs mentioned above are available on the internet from the web site of the National Center for Biotechnology Information (NCBI) or the DNA Data Bank of Japan (DDBJ). The variety of parameters used in making a homology search with the BLAST program are described in detail at those sites. Although the settings of some parameters may be modified as appropriate, homology search is usually performed with default values. Other programs used by skilled artisans for sequence comparison may also be employed.

The above-described Cofilin and their analogous compounds are not limited to those of natural origin. Also useful are those which can be produced by genetic engineering approaches already known in the technical field of the invention, for example, those which are produced by site-directed mutagenesis, random mutagenesis adopting mutagen treatment or PCR misamplification, and cassette mutagenesis. In other words, mutation may have occurred either naturally or by genetic engineering techniques. For instance, Cofilin which is known in terms of amino acid sequence (SEQ ID NO:1) and gene sequence (SEQ ID NO:2) can be produced by established genetic engineering techniques on the basis of those sequences. Applicable genetic engineering techniques are described in, for example, Sambrook and Russel (Molecular Cloning: A Laboratory Manual, 3rd edition (2001)). Skilled artisans can easily prepare those mutated proteins by conventional methods.

Cofilin is referred to by several different names depending upon the species and are usually collectively named as a Cofilin family. In the present invention, all Cofilin molecules including those originating from the species of and belonging to the Cofilin family are collectively referred to as Cofilin. Therefore, in addition to those which is named Cofilin including human nonmuscle-type Cofilin and human muscle-type Cofilin, the Cofilin as referred to in the invention include, for example, porcine destrin, chick actin depolymerizing factor (ADF), depactin from the egg of an urchin, yeast's Abpl, Acanthamoeba's actophorin, and their analogous compounds.

The activity of substances having the Cofilin activity as the promoter of the growth and/or differentiation of hematopoietic stem cells and/or hematopoietic progenitors does not have strict species specificity, as exemplified by the mouse-derived Cofilin showing effect on human cells. Therefore, the active ingredient of the present promoters for the growth and/or differentiation of hematopoietic stem cells and/or hematopoietic progenitors is by no means limited to Cofilin and as long as it is comparable to Cofilin in the activity of promoting the growth and/or differentiation of hematopoietic stem cells and/or hematopoietic progenitors, the active ingredient does not need to originate from any particular species and may originate from various animals including cattle, swine, birds, goats and sheep. It should, however, be noted that for use in humans, human-derived substances having the activity of Cofilin, namely, human-derived Cofilin or human-derived analogous compounds of said Cofilin are preferred.

In one embodiment of the invention, the promoters of the growth and/or differentiation of hematopoietic stem cells and/or hematopoietic progenitors may, in addition to Cofilin or their analogous compounds, contain one or more cytokines as ancillary active ingredients that have the ability to promote the growth and/or differentiation of hematopoietic stem cells and/or hematopoietic progenitors.

Examples of cytokines that can be additionally incorporated as ancillary active ingredients in the present invention include, but are not limited to, interleukin (IL)-1, IL-2, IL-3, IL-4, IL-5, IL-6, IL-7, IL-10 and IL-11, granulocyte colony stimulating factor (G-CSF), granulocyte/macrophage colony stimulating factor (GM-CSF), macrophage colony stimulating factor (M-CSF), erythropoietin (EPO), stem cell factor (SCF), flk-2/flt-3 ligand (FL), thrombopoietin (TPO), basic fibroblast growth factor (bFGF), acidic fibroblast growth factor (aFGF), insulin-like growth factor (IGF), epidermal growth factor (EGF), hepatocyte growth factor (HGF), transforming growth factor-□ (TGF-□), protease nexin I, protease nexin II, platelet-derived growth factor (PDGF), cholinergic differentiation factor (CDF), leukocyte migration inhibitory factor (LIF), etc. If desired, IL-6/soluble IL-6 receptor complex or Hyper IL-6 (fusion protein from IL-6 and soluble IL-6 receptor) may also be incorporated. Cytokines that can be additionally incorporated in the present invention are preferably stem cell factor (SCF), flk-2/flt-3 ligand (FL), thrombopoietin (TPO), and combinations of two or more of these.

If those cytokines are incorporated as ancillary active ingredients, the efficacy of Cofilin as the promoters of the growth and/or differentiation of hematopoietic stem cells and/or hematopoietic progenitors is increased synergistically. The amount of addition of those cytokines is not limited in any particular way but they may, for instance, be added in 0.0001-200000 wt % with human Cofilin taken as 100. The amount of addition of those ancillary active ingredients is by no means limited to the above-noted values and can be determined as appropriate for the symptoms of the disease, the age of the patient, etc. Those cytokines need not necessarily be administered in the same dosage form at the same time as Cofilin and in one illustrative case the administration of a Cofilin may be followed by the administration of a cytokine.

In one embodiment of the present invention, a substance other than Cofilin that has the HPP-CFC activity may be added as a further ancillary active ingredient to the above-described promoters of the growth and/or differentiation of hematopoietic stem cells and/or hematopoietic progenitors. The substance other than Cofilin that has the HPP-CFC activity and which may be added as a further ancillary active ingredient refers to all substances other than Cofilin that are capable of promoting the growth and/or differentiation of hematopoietic stem cells and/or hematopoietic progenitors by promoting the formation of HPP-CFC derived colonies. By administering Cofilin and those additional ancillary active ingredients simultaneously, the action of promoting the growth and/or differentiation of hematopoietic stem cells and/or hematopoietic progenitors can be enhanced synergistically. Such additional ancillary active ingredients include, but are not limited to, SCF, flk2/flt-3 ligand, TPO, IL-6/ soluble IL-6 receptor and Hyper IL-6 (fusion protein from IL-6 and soluble IL-6 receptor).

The promoters of the invention for the growth and/or differentiation of hematopoietic stem cells and/or hematopoietic progenitors which contain Cofilin as an active ingredient are effective, based on the functions they exhibit upon administration into the body, in improving methods for treating diseases that result from insufficient growth and/or differentiation of hematopoietic stem cells and/or hematopoietic progenitors, in particular, panhematopenia and/or diseases that are accompanied by hematopoietic hypofunction, or hematopenia or diseases that are accompanied by impaired hematopoietic function and/or methods of treatment that are accompanied by hematopenia or impaired hematopoietic function. Examples of the diseases mentioned above include Fanconi syndrome, aplastic anemia, cancers such as malignant lymphoma and acute leukemia, chronic hepatopathy, renal failure, patients under massive transfusion, either during operation or of preserved blood, severe infections, myelopathic thrombocytopenia, idiopathic thrombocytopenic purpra (ITP), STE, poisonous snake bite, hemolytic uremic syndrome, sthenia of splenic function, hemorrhage, Barnard-Soulier syndrome, Glanzmann's thrombocytasthenia, uremia, anti-platelet antibodies, myeloproliferative diseases, etc.

The way the present promoters of the growth and/or differentiation of hematopoietic stem cells and/or hematopoietic progenitors are administered is not particularly limited but they are generally administered parenterally as by intravenous, intraperitoneal, intramuscular and other routes. In the present invention, intravenous administration is preferred.

The amount in which the present promoters of the growth and/or differentiation of hematopoietic stem cells and/or hematopoietic progenitors are used as therapeutics or ameliorators varies with the manner of their use, the object of use, etc. In case of administration by injection, the promoters are preferably administered in daily amounts from about 0.002 µg/kg to 20 mg/kg, more preferably from about 0.2 µg/kg to 2 mg/kg as calculated for the amount of protein in human Cofilin.

The present promoters of the growth and/or differentiation of hematopoietic stem cells and/or hematopoietic progenitors may be prepared in either liquid or solid form.

If the present promoters of the growth and/or differentiation of hematopoietic stem cells and/or hematopoietic progenitors are to be prepared in liquid form, Cofilin is first dissolved in solvents such as aqueous solvents (e.g. distilled water), water-soluble solvents (e.g. physiological saline and Ringer solution) and oily solvents (e.g. sesame oil and olive oil) and then worked up by conventional methods. If desired, solubilizing agents (e.g. sodium salicylate and sodium acetate), buffers (e.g. sodium citrate and glycine), isotonization agents (e.g. glucose and invert sugar), stabilizers (e.g. human serum albumin and polyethylene glycol), preservatives (e.g. benzalkonium chloride and phenol), soothing agents (e.g. benzyl alcohol and procaine hydrochloride), and other additives may be added. The pH of the prepared aqueous solutions is preferably adjusted to about 3-8, more preferably to about 5-7. Adjustment to the stated pH ranges can be accomplished by adding, for example, dilute acids (e.g. dilute hydrochloric acid) and dilute alkalis (e.g. dilute sodium hydroxide and dilute sodium hydrogencarbonate).

When making pharmaceutical preparations from the present promoters of the growth and/or differentiation of hematopoietic stem cells and/or hematopoietic progenitors, one may incorporate human serum albumin (HAS) as a stabilizer in Cofilin-containing solution preparations so that they are adjusted to show pH 3-8 in solution form. This procedure is preferred since it causes only small drop in activity of Cofilin not only during storage but also in the freezing or freeze-drying process, and because it allows frozen preparations to be thawed into a clear solution. HSA may be of any type but in order to put the present invention to clinical application, HSA is preferably of such a quality as to permit parenteral administration. For example, the plasma of healthy persons may be fractionated and purified by the sixth method of Cohn's ethanol fractionation to prepare a useful HAS. Acetyltryptophan sodium and sodium caprylate may also be contained as stabilizers. When the respective components are made into aqueous solution, HSA is preferably contained in amounts from about 0.1 mg to about 50 mg, particularly from about 0.5 mg to about 20 mg per milliliter of the aqueous solution.

When making pharmaceutical preparations from the present promoters of the growth and/or differentiation of hematopoietic stem cells and/or hematopoietic progenitors, one may, in addition to the above-described HAS, incorporate one or more compounds to Cofilin-containing solution preparations as selected from the group consisting of amino acids such as glycine, glutamic acid, aspartic acid, alanine and praline, in particular, monoamino-type aliphatic amino acids or cyclic amino acids, monosaccharides such as glucose and mannose, sugar alcohols such as sorbitol and mannitol, physiologically acceptable salts thereof and derivatives thereof. When Cofilin is made into aqueous solution, the above-mentioned compounds are preferably incorporated in amounts from about 10 mg to 100 mg (if they are monosaccharides or sugar alcohols), and from about 5 mg to 50 mg (if they are amino acids) per milliliter of the aqueous solution. In the process of making pharmaceutical preparations, the aqueous solution is so adjusted that, when taken as such, it shows a pH of from about 3 to 8, preferably from 5 to 7. If acidic amino acids such as glutamic acid are to be incorporated, adjustment to the specified pH can be achieved by adding them in the amounts specified above. Alternatively, if desired or in the case where no acidic amino acids are incorporated, adjustment to the specified pH can be achieved using mineral acids such as hydrochloric acid and phosphoric acid or buffers such as succinic acid, tartaric acid and citric acid.

The present promoters of the growth and/or differentiation of hematopoietic stem cells and/or hematopoietic progenitors can be prepared in solid form by, for example, freezing or freeze-drying Cofilin. In particular, from the viewpoints of ease of handling and storage stability, freeze-drying of Cofilin is preferred. In order to prepare the present promoters of the growth and/or differentiation of hematopoietic stem cells and/or hematopoietic progenitors by freezing, promoters prepared as aqueous solution for promoting the growth and/or differentiation of hematopoietic stem cells and/or hematopoietic progenitors are used as a starting material and typically frozen at about −80° C. to −20° C. The frozen compositions are stored at about −80° C. to 25° C., preferably at about −80° C. to 15° C., more preferably at about −80° C. to −10° C. In order to prepare the present promoters of the growth and/or differentiation of hematopoietic stem cells and/or hematopoietic progenitors by freeze-drying, the frozen compositions described above may be dried under reduced pressure in the usual manner or, alternatively, the above-mentioned aqueous solution or an aqueous solution obtained by thawing the above-described frozen composition is optionally divided into smaller portions, then frozen in the manner described above and dried under reduced pressure in the usual manner.

In the present invention, Cofilin in solid form (e.g. in powder) may be mixed with diluents (e.g. distilled water, physiological saline and glucose), vehicles (e.g. carboxymethyl cellulose (CMC) and sodium alginate), preservatives (e.g. benzalkonium chloride and phenol), soothing agents (e.g. glucose, benzyl alcohol and procaine hydrochloride), etc.

If the above-described solid pharmaceutical preparations are made by freeze-drying, they may be further processed into solution preparations by dissolving them in suitable solvents just prior to use. More specifically, the above-described solid pharmaceutical preparations are dissolved in distilled water, physiological saline or the like and used as solution preparations. If desired, the solid pharmaceutical preparations may be used after they are solubilized with pH-adjusted solubilizers containing the above-mentioned monosaccharides, sugar alcohols, amino acids, etc.

If the present promoters of the growth and/or differentiation of hematopoietic stem cells and/or hematopoietic progenitors are to be produced either as solution preparations or by freezing, Cofilin-containing aqueous solutions may preferably be sterilized by filtration or the like. If the promoters are to be produced as solution preparations, the sterilized aqueous solution can be used as such; if the promoters are to be produced by freezing, the sterilized solution may be frozen.

If the present promoters of the growth and/or differentiation of hematopoietic stem cells and/or hematopoietic progenitors are to be produced by freeze-drying, Cofilin-containing aqueous solutions may preferably be sterilized by filtration or the like or, alternatively, the thus sterilized aqueous solution is aseptically dispensed into vials and the like in smaller portions before it is subjected to the above-mentioned freeze-drying treatment. In this case, the head space of each vessel may be rendered vacuum or purged with nitrogen gas in order to enhance the stability of the composition in the vessel. If the freeze-dried products are to be dissolved in aqueous solutions containing amino acids, monosaccharides or sugar alcohols, such aqueous solutions are preferably sterilized by filtration, then aseptically dispensed into ampules and the like in smaller portions before they are sterilized with steam in the usual manner.

Since the present promoters of the growth and/or differentiation of hematopoietic stem cells and/or hematopoietic progenitors which contain Cofilin as an active ingredient exhibit the above-described pharmacological effects, the present promoters of the growth and/or differentiation of hematopoietic stem cells and/or hematopoietic progenitors may also be used in regenerative medicine.

If the present promoters of the growth and/or differentiation of hematopoietic stem cells and/or hematopoietic progenitors are to be used in regenerative medicine, they are either administered in vivo as described above or added ex vivo to a culture medium. If the growth and/or differentiation promoters of the present invention are to be used ex vivo, the following method may typically be employed but any other methods that are known in the technical field of interest may also be adopted. In the first step, hematopoietic stem cells and/or hematopoietic progenitors are collected from a subject by a method known in the technical field of interest and then grown by culture in a culture medium containing the growth and/or differentiation promoters of the present invention, thereby promoting the growth and/or differentiation of hematopoietic stem cells and/or hematopoietic progenitors; thereafter, the grown and/or differentiated hematopoietic stem cells and/or hematopoietic progenitors are transferred back into the subject.

If the growth and/or differentiation promoters of the present invention are to be used ex vivo, they are added to a liquid culture medium in such amounts that the Cofilin concentration in the medium ranges from 1 ng/ml to 100 µg/ml, preferably from 2.5 ng/ml to 50 µg/ml, more preferably from 25 ng/ml to 10 µg/ml, most preferably from 250 ng/ml to 2.5 µg/ml. As mentioned earlier, cytokines may further be added to the growth and/or differentiation promoters of the present invention. Cytokines that may be optionally added in the invention are preferably stem cell factor (SCF), flk-2/flt-3 ligand (FL), thrombopoietin (TPO) and combinations of two or more of these.

(1) Method of Assaying the Substance having the Activity of Promoting the Growth and/or Differentiation of Hematopoietic Stem Cells and/or Hematopoietic Progenitors In order to assay the growth of hematopoietic stem cells and/or hematopoietic progenitors, the invention uses a method comprising the steps of performing liquid culture on a sample and mouse bone marrow cells removed of cells that have expressed lineage markers and counting the number of high proliferative potential colony forming cells (HPP-CFC) present in the conditioned medium including the hematopoietic stem cells. Assay systems using HPP-CFC as an indicator are widely employed in studies of hematopoietic stem cells. For example, the stem cell factor (SCF) acting on hematopoietic stem cells is purified with reference to HPP-CFC.

(2) Purification of the Substance having the Activity of Promoting the Growth and/or Differentiation of Hematopoietic Stem Cells and/or Hematopoietic Progenitors In order to purify the substance having the activity of promoting the growth of hematopoietic stem cells and/or hematopoietic progenitors, a protein-free culture supernatant of S6 cells (600 L) and cells are used as starting materials and concentrated (to 18 L) by ultrafiltration through an UF membrane having a molecular weight of 10000, followed by sequential combinations of treatments including precipitation with 50% ammonium sulfate and various column chromatographic processes using phenyl-Sepharose (Amersham Pharmacia Biotech K.K.), heparin-Sepharose (Amersham Pharmacia Biotech K.K.), chelate-Sepharose (Amersham Pharmacia Biotech K.K.), MonoS (Amersham Pharmacia Biotech K.K.), gel filtration, etc. Proteins are verified by absorbance at 280 nm, Lowry quantitation, and SDS-PAGE.

(3) Determining the Structure of the Substance having the Activity of promoting the Growth and/or Differentiation of Hematopoietic Stem Cells and/or Hematopoietic Progenitors In order to determine the structure of the substance having the activity of promoting the growth of hematopoietic stem cells and/or hematopoietic progenitors, a protein/nucleic acid sequence database is searched through with reference to the molecular weights of a number of peptide fragments that result from limited decomposition of proteins and to the molecular weights that result from their collision-induced dissociation and the initial protein is identified. The technical background of this method comprises the following three aspects: the advances of mass spectrometer and mass spectrometry that make it possible to determine the molecular weights of proteins and peptides with high precision; (2) the Genome Project and other technological efforts have accumulated huge volumes of protein/nucleic acid sequence data; and (3) the evolution of computer technology that can process high volumes of data at high speed. The advantage of the method is that very small amounts (~10 ng plus) of samples are processed by simple procedures to enable rapid and positive identification of unknown proteins.

(4) Method of Measuring HPP-CFC Activity

Measurement of HPP-CFC activity is performed by the following procedure: with a view to obtaining hematopoietic stem cells specifically, T cells, B cells, granulocytes and macrophages were removed from anti-cancer agent 5-fluorouracil treated murine bone marrow cells to prepare hematopoietic stem cell fractions; after adding a sample and cytokines, the hematopoietic stem cell fractions are subjected to liquid culture and part of the conditioned medium including the hematopoietic stem cells is subjected to colony assay; the number of the resulting macroscopic HPP-CFC colonies is counted.

Whenever necessary in the present specification, bases, amino acids, etc. are indicated by abbreviations according to IUPAC-IUB Commission on Biochemical Nomenclature or conventional abbreviations in the art of interest.

On the pages that follow, examples are described. They are provided only for illustrating the present invention in greater detail and are by no means intended to limit the scope of the invention.

EXAMPLES

Example 1

Purification and Identification of the Substance having the Activity of Promoting the Growth and/or Differentiation of Hematopoietic Stem Cells and/or Hematopoietic Progenitors (1) Preparation of Human S6 Cells Human S6 cells were cultured in roller bottles (Corning, 430851) having an effective area of 750 cm$^2$. Specifically, $1 \times 10^8$ cells were planted in each roller and cultured in 500 ml of an F-12 medium (Flow Laboratories) supplemented with 10% fetal bovine serum (FBS, Hyclone) at 37° C. for 72 hours at 0.5 rpm. After 72 hr culture, the culture supernatant was spun off and washed with phosphate buffered saline (PBS, Nissui Seiyaku Co., Ltd.) three times. After the washing, the cell pellet cleared of the supernatant by centrifugation was stored frozen at −20° C.

(2) Assaying the Substance having the Activity of Promoting the Growth and/or Differentiation of Hematopoietic Stem Cells and/or Hematopoietic Progenitors using Mouse Bone Marrow Cells The activity of the substance capable of promoting the growth and/or differentiation of hematopoietic stem cells and/or hematopoietic progenitors was measured by the following procedure: with a view to obtaining hematopoietic stem cells specifically, T cells, B cells, granulocytes and macrophages were removed from anti-cancer agent 5-fluorouracil (KYOWA HAKKO KOGYO Co., Ltd.) treated murine bone marrow cells to prepare hematopoietic stem cell fractions; after adding a sample and cytokines, the hematopoietic stem cell fractions were subjected to liquid culture and part of the conditioned medium including the hematopoietic stem cells was subjected to colony assay; and the number of the resulting macroscopic HPP-CFC colonies was counted. This procedure is hereunder referred to as the method of determining HPP-CFC activity.

Specifically, mice DBF1 (female, 10-15 weeks old, purchased from Charles River Japan Inc.) were administered 5-fluorouracil (150 mg/kg, i.v., KYOWA HAKKO KOGYO Co., Ltd.) and 2 days later, bone marrow cells were collected from the femoral bones. The collected bone marrow cells were labelled with rat anti-mouse CD4 antibody (CALTAG), CD8 antibody (CALTAG), B220 antibody (CEDERLANE), Gr-1 antibody (CEDERLANE), and Mac-1 antibody (CALTAG). Those rat antibodies were all IgG. Following the reaction with goat anti-rat IgG antibody labelled Dyna Beads (DYNAL), the cells binding to the Dyna Beads were removed magnetically to obtain lineage marker negative bone marrow cells (Lin⁻ BMCs). The Lin⁻ BMCs were adjusted to a concentration of $2.5 \times 10^4$ cells/ml in an α-MEM medium (Invitrogen) supplemented with 10% FCS (Invitrogen). To the cell suspension, mouse IL-3 (at a final concentration of 10 ng/ml, INTERGEN) was added and the mixture was put into each well on a 24-well plate (Corning) in a respective amount of 1 ml. Subsequently, a sample was put into each well and cultured in a CO$_2$ incubator under conditions of 37° C. and 5% CO$_2$. At days 6 and 10 of liquid culture, the cultured cells in each well were suspended and 200 μl of the cell suspension was collected. In a 15-ml centrifugal tube, the collected cell suspension (200 μl) was mixed with 1.5 ml of FCS (at a final concentration of 30%), 0.5 ml of BSA (at a final concentration of 1%, ICN), 50 μl of 2-ME (at a final concentration of $1 \times 10^{-4}$ M, Wako Pure Chemical Industries, Ltd.), 2 ml of 2.5% methyl cellulose prepared in α-MEM (at a final concentration of 1%, Shin-Etsu Chemical Co., Ltd.), 50 μl of each hematopoietic factor (i.e., mouse IL-3 (INTERGEN), SCF (PeproTech), human IL-6 (PeproTech), G-CSF (CHUGAI PHARMACEUTICAL CO., LTD.) and M-CSF (The Green Cross Corp.); all at a final concentration of 10 ng/ml) and 0.5 ml of α-MEM, making a total of 5 ml. Thereafter, the mixture was left to stand for 20 minutes to remove all bubbles and 1 ml of it was transferred into four 35-mm dishes (Corning) for cultivating suspended cells. Two 35-mm dishes were put into a 9-cm Petri dish and an uncapped 35-mm dish filled with distilled water was also put in for 14 days of culture in a CO$_2$ incubator under conditions of 37° C. and 5% CO$_2$. The number of colonies larger than 2 mm in diameter was counted as HPP-CFC.

(3) Purifying the Substance having the Activity of Promoting the Growth and/or Differentiation of Hematopoietic Stem Cells and/or Hematopoietic Progenitors To S6 cells (wet weight, 269 g) that had been washed with PBS and stored frozen, 20 mM Tris/HCl buffer (pH 7.0) was added and the mixture was disrupted with a Potter-Elvehjem type Teflon (registered trademark) homogenizer (IWAKI GLASS CO., LTD.). The cell residue was removed by centrifugation (8000 rpm, 20 min) to give a supernatant, which was rendered 50% saturated by addition of ammonium sulfate. The supernatant was then loaded on phenyl-Sepharose (Amersham Pharmacia Biotech K.K.) equilibrated with 2 M ammonium sulfate/20 mM Tris/HCl buffer (pH 7.0) and washed thoroughly; thereafter, the concentration of ammonium sulfate was lowered progressively to 1.5 M, 1 M, 0.5 M and 0 M for eluting the corresponding bound fractions. The factor of interest, namely, S6 factor already described in this specification, had been mostly eluted into the 1 M ammonium sulate/20 mM Tris/HCl buffer (pH 7.0) fraction, as verified by the same approach as the method of determining HPP-CFC activity described in (2) above.

The active fractions obtained on phenyl-Sepharose were fully dialyzed against 0.6 M NaCl/20 mM Tris/HCl buffer (pH 7.0), loaded onto a heparin-Sepharose column (Amersham Pharmacia Biotech K.K.) for washing and thereafter treated with 2 M NaCl/20 mM Tris/HCl buffer (pH 7.0) to elute the respective bound fractions. Each of the heparin eluted fractions was diluted 4-fold with 20 mM Tris/HCl buffer (pH 7.0), adsorbed on a copper (Cu) chelate-Sepharose column (Amersham Pharmacia Biotech K.K.) equilibrated with 0.5 M NaCl/20 mM Tris/HCl buffer (pH 7.0), and subjected to buffer replacement through two-stage washing with 0.5 M and 0.3 M NaCl/20 mM sodium phosphate buffer (pH 6.8).

The bound fractions were eluted with 0.1 M imidazole/0.3 M NaCl/20 mM sodium phosphate buffer (pH 6.8) and, as such, were loaded onto a MonoS ion-exchange column equilibrated with 0.4 M NaCl/20 mM sodium phosphate buffer (pH 6.8) so as to perform 0.4-2 M NaCl gradient elution at a flow rate of 0.7 ml/min, and the eluates were stored after adding a surfactant CHAP to give a final concentration of 0.1%. The HPP-CFC activity was observed in fractions 47-50. It was verified by ELISA that those fractions contained both the desired S6 factor and basic FGF. The MonoS active fractions were divided into two groups, the first group consisting of fractions 47 and 48 and the second group consisting of fractions 49 and 50, and an attempt was made to clear them of the basic FGF by gradient chromatography on a heparin column. After loading on a heparin-Sepharose column equilibrated with 0.4 M NaCl/20 mM sodium phosphate buffer (pH 6.8)/0.1% CHAPS, 0.4-4 M NaCl gradient elution was performed at a flow rate of 0.7 ml/min.

The first MonoS active group showed activity in fractions 30-32; by ELISA, they were verified to possess basic FGF, thus making it clear that the activity of interest derived from basic FGF.

The second MonoS group showed HPP-CFC activity in fractions other than fractions 30-32 (basic FGF fractions), namely, in fractions 22 and 23 where basic FGF was not detected by ELISA. The fractions in the neighborhood of the active fractions were subjected to a dose assay and an assay in a system supplemented with 1 ng/ml of basic FGF. The activity was observed in fractions 22 and 23 in a dose-dependent manner and higher HPP-CFC colony formation promoting activity was shown at day 10 of liquid culture than at day 6. In the basic FGF supplemented assay system, fractions 22 and 23 were also found to have HPP-CFC activity surpassing the full activity of basic FGF taken alone.

For reconfirmation of the activity, another chromatographic run was made on a heparin column with a varied gradient slope. After loading onto a heparin-Sepharose column equilibrated with 0.3 M NaCl/20 mM sodium phosphate buffer (pH 6.8)/0.1% CHAPS, NaCl gradient elution was performed at a milder slope of 0.3-2 M. The HPP-CFC activity was observed in fractions 25-27, which were verified by ELISA to be free of basic FGF. Active fraction 26 was found to possess the activity in a dose-dependent manner and the basic FGF supplemented system also possessed an HPP-CFC activity surpassing the full activity of basic FGF taken alone. A 20 kDa band was also observed in the active fractions by SDS-polyacrylamide electrophoretic analysis (gel density: 10-20% gradient).

As a result of the foregoing steps, fractions showing a 20 kDa band in SDS-polyacrylamide electrophoretic analysis were obtained in an amount of about 0.4 µg from 120 L of S6 cells. Since those fractions were verified to have HPP-CFC activity, the 20 kDa band observed in them was obviously the substance having the activity of promoting the growth and/or differentiation of hematopoietic stem cells and/or hematopoietic progenitors.

(4) Properties of the Substance having the Activity of Promoting the Growth and/or Differentiation of Hematopoietic Stem Cells and/or Hematopoietic Progenitors The factor of interest has the following properties.

1. Molecular Weight: ca. 20 kDa (SDS-PAGE)

The factor was detected as a single band near 20 kDa in SDS-polyacrylamide electrophoretic analysis, with no difference in motility irrespective of whether the condition was reducing or non-reducing. Hence, the factor had no intermolecular disulfide bonds.

2. Isoelectric Point: 8.1±0.5

The factor was detected as a spot in the stated range in two-dimensional electrophoretic analysis using AFB Multiphor II (Amersham Pharmacia Biotech K.K.).

(5) Determining the Structure of the Substance having the Activity of Promoting the Growth and/or Differentiation of Hematopoietic Stem Cells and/or Hematopoietic Progenitors An attempt was made to determine the structure of the factor by the following procedure.

Preparing Samples for MS and MS/MS Measurements

Purified fractions containing the 20 kDa band identified as the factor of interest were subjected to SDS-polyacrylamide electrophoretic analysis on a 12.5% acrylamide gel and thereafter stained with 0.1% CBB/40% MeOH/1% AcOH. After being detected, the 20 kDa band was sliced and discolored with 40% MeOH/1% AcOH. The discolored gel was immersed in 10 mM DTT/100 mM $NH_4CHO_3$ (pH 8.7), incubated at 56° C. for 1 hour, supplemented with 55 mM iodoacetamide and incubated in the dark for 45 minutes to reduce and alkylate the factor. After removing the excess reducing and alkylating agents from the gel, 150 mg of trypsin (Promega)/5 mM $CaCl_2$/50 mM $NH_4HCO_3$ was added and trypsin digestion within the gel was performed at 37° C. for 18 hours. After the end of the reaction, the mixture of peptide fragments was extracted and dried with SPEED BACK (Savant). The peptide fragment mixture dissolved in 0.05% TFA was subjected to PorosR2 (Perseptive Co., Ltd.) equilibrated with 0.05% TFA and desalted by elution with 50% MeOH/0.2% FA. The desalted peptide fragment mixture was used as a sample (conditioned peptide fragment compound) for each of mass spectrometry (MS) and tandem mass spectrometry (MS/MS). As a negative control, a site from which a 20 kDa band would be detectable was sliced out of the lanes subjected to SDS-polyacrylamide electrophoretic analysis with a sample buffer only and conditioned by the same method as was the factor of interest. For operating details other than those described above, refer to the method of Wilm et al. (Wilm, M., Shevchenko, A., Houthaeve, T., Breit, S., Schweigerer, L., Fotsis, T. and Mann, M., Nature 379, 466-469, 1996).

Structural Determination by MS and MS/MS Analyses

To determine the structure of the factor, Q-TOF (quadrupole orthogonal acceleration time-of-flight mass spectrometer of Micromass Inc.) was used and MS and MS/MS were performed in accordance with the operating manuals. First, the conditioned peptide fragment mixture and the negative control were measured over a mz range of 100-1500 by MS. For polyvalent molecular ions serving as a peptide indicator, comparison was made by the two methods and three divalent molecular ions were detected significantly in the conditioned peptide fragment mixture (see Table 1).

TABLE 1

Major Ions Obtained in MS and MS/MS Analyses

| | |
|---|---|
| Molecular ion number: 1 | Molecular ion: 583.82 (divalent) |
| Molecular ion number: 2 | Molecular ion: 669.39 (divalent) |
| | Product ion (y ion): 712.43, 827.45, 990.51, 1103.60, 1174.66 |
| | Product ion (i ion): 86.08, 136.07 |
| Molecular ion number: 3 | Molecular ion: 670.9 (divalent) |

Those three divalent molecular ions were chosen individually and analyzed by MS/MS. On the basis of the obtained information about the major product ions, the inventors made a search using ProteinProspector, one of the database search programs published on the internet, and hit on the human nonmuscle-type Cofilin (AC: P23528, pI 8.22, 166aa), well known as low-molecular weight actin regulating protein. The factor of interest was similar to the human nonmuscle-type Cofilin in such terms as molecular weight and isoelectric point.

However, given the results of MS and MS/MS analyses alone, it is difficult to conclude positively that the factor of interest is a human nonmuscle-type Cofilin. Hence, in order to make a close study on the match between the information described in Table 1 and the human nonmuscle-type Cofilin, peptides were synthesized (see Table 2) as inferred from the obtained information and their identity was verified by measuring the spectra for collision-induced dissociation. As it turned out, all of the information obtained was in agreement with the information described in Table 1. It is worth special mention that the obtained information contained information about the peptides having N and C terminals that is given in Table 2, thus indicating that the N and C terminals in the factor are identical to those in the human nonmuscle-type Cofilin. On the basis of those findings, the factor was identified as a human nonmuscle-type Cofilin (of active type from the viewpoint of actin regulation) that had been cleared of the methionine at the start of translation, with the ensuing alanine being acetylated and the subsequent serine not phosphorylated (see FIG. 1).

TABLE 2

Partial Amino Acid Sequences Inferred by Database Search

Molecular ion number: peptide having an N terminal as inferred from information 1
(AcetN)ASGVAVSDGVIK (SEQ ID NO: 5) + added Na
Molecular ion number: peptide as inferred from information 2
YALYDATYETK (SEQ ID NO: 6)
Molecular ion number: peptide having a C terminal as inferred from information 3
LGGSAVISLEGKPL (SEQ ID NO: 7)

Example 2

Preparation of Cofilin (1) Preparation of a cDNA Library Derived from Human S6 Cell Line S6 cells ($1.2 \times 10^8$ cells) were cultured for 4 days in a roller bottle containing a serum-free medium F12 (Invitrogen) and 37 μg of S6 cell-polyA RNA was prepared from the cultured cells using FastTrack mRNA Isolation Kit (Invitrogen). From 5 μg of the S6 cell-polyA RNA, cDNA having an EcoRI (Takara Shuzo Co., Ltd.) restriction enzyme site and a NotI (Takara Shuzo Co., Ltd.) restriction enzyme site at opposite ends was prepared using TimeSaver cDNA Synthesis Kit (Amersham Pharmacia Biotech K.K.) and Directional Cloning Toolbox (Amersham Pharmacia Biotech K.K.).

Then, the cDNA was inserted into the □ phage cloning vector □ Excell NotI/EcoRI/CIP (Amersham Pharmacia Biotech K.K.) and in vitro packaging was effected using Gigapack III Gold Packaging Extract (Stratagene). Using *E. coli* NM522 (Stratagene) as a host, the number of plaques was counted on an agar medium to determine the titer, which was calculated to be $1.37 \times 10^6$ pfu. Further, using *E. coli* NM522 as a host, library amplification was effected to prepare an S6 cell cDNA library having a titer of $6.9 \times 10^{10}$ pfu/ml. The S6 cell cDNA library had an average insertion size of 1.0 kb.

(2) Full-Length Cloning of Human Nonmuscle-Type Cofilin cDNA by PCR

On the basis of the base sequence (AC: D00682, 501 bp) coding for the amino acid sequence of a placenta derived human nonmuscle-type Cofilin, oligomers SK013 (corresponding to Nos. 1-16 in FIG. 2; primer SK013: SEQ ID NO:3) and SK014 (corresponding to Nos. 476-501 in FIG. 2; primer SK014: SEQ ID NO:4) were synthesized.

(SEQ ID NO:3)
Primer SK013 5'-ATGGCCTCCGGTGTGGCTGTCTCTGA-3'

(SEQ ID NO:4)
Primer SK014 5'-TCACAAAGGCTTGCCCTCCAGGGAGA-3'

Human nonmuscle-type Cofilin cDNA was amplified by PCR using Advantage 2 polymerase (CLONTECH), with the S6 cell cDNA library being used as a template and primer SK013 (SEQ ID NO:3) and primer SK014 (SEQ ID NO:4) as primers. The amplified products were subcloned to pCR-Blunt II-TOPO vector using Zero Blunt TOPO PCR Cloning Kit (Invitrogen) to give positive clones having DNA fragments of about 500 base pairs. The positive clones were subjected to a base sequence analysis with ABI PRISM 310 (Applied Biosystems) using BigDye Terminator Cycle Kit (Applied Biosystems), ascertaining the acquisition of a full-length nonmuscle-type Cofilin cDNA of 501 base pairs. The base sequence of the S6 cell derived human nonmuscle-type Cofilin cDNA was different from that of the placenta derived human nonmuscle-type Cofilin cDNA at two bases but neither was accompanied by an amino acid mutation (see FIG. 3).

(3) Constructing an Expression Vector for human Nonmuscle-Type Cofilin cDNA

The nonmuscle-type Cofilin cDNA clones and a pDE vector derived from pKDEMSS vector (Kitano K, Fukuda Y, Nagahira K, Nasu T, Izumi R, Kawashima K, and Nakanishi T; Immunol. Lett. 47, 215-222, 1995) were digested with EcoR I and dephosphorylated with an alkali phosphatase (Takara Shuzo Co., Ltd.). Thereafter, an EcoR I fragment containing the nonmuscle-type Cofilin cDNA and the pDE vector's DNA fragment were subjected to agarose gel electrophoresis and a DNA containing gel was sliced and purified by CONCERT Rapid Gel Extraction System (Invitrogen). Using DNA Ligation Kit (Takara Shuzo Co., Ltd.), the nonmuscle-type cDNA fragment of Cofilin was inserted into the pDE vector's DNA fragment and used to transform *E. coli* JM109 (Toyobo Co., Ltd.), thereby preparing an expression vector for the human nonmuscle-type Cofilin. It was verified by a restriction enzyme that the human nonmuscle-type Cofilin cDNA inserted into the expression vector was oriented in a forward direction relative to the expression promoter.

(4) Expressing the Human Nonmuscle-Type Cofilin in COS-1 Cells

The recombinant nonmuscle-type Cofilin was expressed and its expression verified by the following procedure.

Expressing the Human Nonmuscle-Type Cofilin in COS-1 Cells

Using the human nonmuscle-type Cofilin cDNA expression vector, the human nonmuscle-type Cofilin was expressed in animal cells and a check was made to see whether the expressed protein had HPP-CFC activity. Using COS-1 cells as host animal cells (purchased from the Institute of Physical and Chemical Research), the human nonmuscle-type Cofilin cDNA expression vector was transfected by the lipofectin technique. Specifically, $1 \times 10^6$ COS-1 cells were planted on 10-cm culture dishes (Corning, 430167). The medium was a Dulbecco's minimum essential medium containing 10% fetal bovine serum (DMEM, NIS-SUI PHARMACEUTICAL CO., LTD.). On the next day, the cells were rinsed once with 5 ml of Opti-MEM I medium (Invitrogen) and after adding 5 ml of Opti-MEM I medium, the cells were cultured at 37° C. for 2 hours. After 2-hr culture, a liquid mixture of 1 µg of the expression plasmid prepared in Example 2(3) and 10 µg of lipofectin (Invitrogen) was added and culture was effected for an additional 5 hours at 37° C. After the culture, 5 ml of Opti-MEM medium was added to make a total of 10 ml and culture was effected for 72 hours at 37° C. in the presence of 5% $CO_2$. After the 72-hr culture, the culture supernatant was recovered by centrifugation. As a negative control, the initial expression vector having no insert of the human nonmuscle-type Cofilin was used and subjected to the same process of expressing.

Detecting Secretory Recombinant Human Nonmuscle-Type Cofilin

Culture supernatant analysis by SDS-polyacrylamide electrophoresis showed that the culture supernatant transfected with the human nonmuscle-type Cofilin cDNA expression vector had a significantly visible 20 kDa band that was believed to be the recombinant human nonmuscle-type Cofilin. In western blot analysis, the 20 kDa band reacted specifically with a rabit anti-human nonmuscle-type Cofilin peptide (13-22) polyclonal antibody (Cytoskeleton). Secretion of the recombinant human nonmuscle-type Cofilin was therefore verified. By western blot analysis and SDS-polyacrylamide electrophoretic analysis, the secretory recombinant human nonmuscle-type Cofilin was found to have been expressed in an amount of 2.5 µg per ml.

Detecting Secretory Natural Human Nonmuscle-Type Cofilin

A culture supernatant transfected with the initial expression vector (pDE vector) having no insert of the human nonmuscle-type Cofilin was allowed to precipitate by addition of 10% trichloroacetic acid and 100 volumes of the precipitate were subjected to western blot analysis in the same manner as described above; a weak band of natural human nonmuscle-type Cofilin was detected. This fact shows that the nonmuscle-type Cofilin heretofore believed to occur solely in cells also occur as a secretory type in very small amounts.

Example 3

Verifying the Activity of Recombinant Human Nonmuscle-Type Cofilin as the Substance having the Activity of Promoting the Growth and/or Differentiation of Hematopoietic Stem Cells and/or Hematopoietic Precursor Cells In order to know whether the secretory recombinant human nonmuscle-type Cofilin that was expressed in COS-1 cells was the substance having the activity of promoting the growth and/or differentiation of hematopoietic stem cells and/or hematopoietic progenitors, an HPP-CFC assay was performed on the culture supernatant.

Mice DBF1 (female, 10-15 weeks old, purchased from Charles River Japan Inc.) were administered 5-fluorouracil (150 mg/kg, i.v., KYOWA HAKKO KOGYO Co., Ltd.) and 2 days later, bone marrow cells were collected from the femoral bones. The collected bone marrow cells were labelled with rat anti-mouse CD4 antibody (CALTAG), CD8 antibody (CALTAG), B220 antibody (CEDERLANE), Gr-1 antibody (CEDERLANE), and Mac-1 antibody (CALTAG). Those rat antibodies were all IgG. Following the reaction with goat anti-rat IgG antibody labelled Dyna Beads (DYNAL), the cells binding to the Dyna Beads were removed magnetically to obtain lineage marker negative bone marrow cells (Lin⁻ BMCs). Those cells were used in HPP-CPC assay as hematopoietic stem cell fractions.

The obtained hematopoietic stem cell fractions were adjusted to a concentration of $2.5 \times 10^4$ cells/ml in an □-MEM medium supplemented with 10% FCS. To the cell suspension, mouse IL-3 (at a final concentration of 10 ng/ml) was added and the mixture was put into each well on a 24-well culture plate (Corning) in a respective amount of 1 ml. Further, the Cofilin culture supernatant prepared in Example 2 or a cytokine was added to each well and subjected to liquid culture. A portion of the conditioned medium including the hematopoietic stem cells was subjected to colony assay and the number of the resulting macroscopic HPP-CFC colonies was counted to determine the HPP-CFC activity.

In FIG. 4, Cofilin 1, 2, 3 and 4 refer to 1-, 10-, 100- and 1000-fold dilutions, respect of the 10-fold concentration of the Cofilin culture supernatant. Since in Example 2, the secretory recombinant human nonmuscle-type Cofilin was expressed in an amount of 2.5 µg per ml, the α-MEM medium for liquid culture having a tenth volume of the diluted Cofilin culture supernatant added thereto contained Cofilin 1, Cofilin 2, Cofilin 3 and Cofilin 4 in respective amounts of 2500 ng/ml, 250 ng/ml, 25 ng/ml and 2.5 ng/ml as the concentration of recombinant human Cofilin. Further referring to FIG. 4, C1 and C2 represent the wells to which PBS was added in the same amount as the diluted Cofilin culture supernatant. SCF1, SCF5 and SCF10 mean that the medium for liquid culture contained SCF in respective amounts of 1 ng/ml, 5 ng/ml and 10 ng/ml. The data in FIG. 4 show the number of HPP-CFC colonies in 200 µl of the cell suspension in each well at days 6 and 10 of liquid culture. Input refers to the number of HPP-CFC colonies in 200 µl of the cell suspension before liquid culture.

Compared to the negative control, the recombinant human nonmuscle-type Cofilin showed the HPP-CFC activity in a significant concentration-dependent manner that was characteristic of the factor of interest whose activity at day 10 of liquid culture tended to be higher than at day 6 (see FIG. 4). The concentration at which the activity was observed was about 25 ng/ml (noted by Cofilin 3 in FIG. 4), which was comparable to 1 ng/ml of SCF (noted by SCF1 in FIG. 4). The secretory natural human nonmuscle-type Cofilin was observed in the culture supernatant of the negative control, suggesting that said Cofilin was responsible to some extent for the HPP-CFC activity (FIG. 4).

By means of the process described above, the inventors found that the human nonmuscle-type Cofilin well known as a low-molecular weight actin regulating protein would act as the substance having the activity of promoting the growth and/or differentiation of hematopoietic stem cells and/or hematopoietic progenitors.

Example 4

Evaluating the Activity of Recombinant Human Nonmuscle-Type Cofilin in Promoting the Growth of Human Hematopoietic Stem Cells and/or Hematopoietic Progenitors (CD34 Positive Cells)

In order to know whether the recombinant human nonmuscle-type Cofilin had the activity of promoting the growth of human hematopoietic stem cells and/or hematopoietic progenitors, the inventors made an experiment in which the recombinant human nonmuscle-type Cofilin containing culture supernatant of COS-1 cells that was prepared in Example 2 was added during culture of human hematopoietic stem cells.

To human umbilical cord blood, a silica gel suspension was added to give 10% (v/v) and the mixture was stirred gently and then left to stand at 37° C. for about 1 hour. After overlaying on lymphoprep (NYCOMED) having a specific gravity of 1.077, specific gravity centrifugation was performed at 1600 rpm for 30 minutes to obtain mononuclear cells fraction. Subsequently, CD34 positive cells were acquired using Direct CD34 Progenitor Cell Isolation Kit and Auto-MACS (Miltenyi Biotec). The thus obtained CD34 positive cells were adjusted to a concentration of $1 \times 10^4$ cells/ml in an □ MEM (GIBCO) medium supplemented with 20% FCS (CCT) and 1% BSA (SIGMA) and were added to a 12-well culture plate (Falcon) in respective amounts of 1 ml/well.

Figure 5:
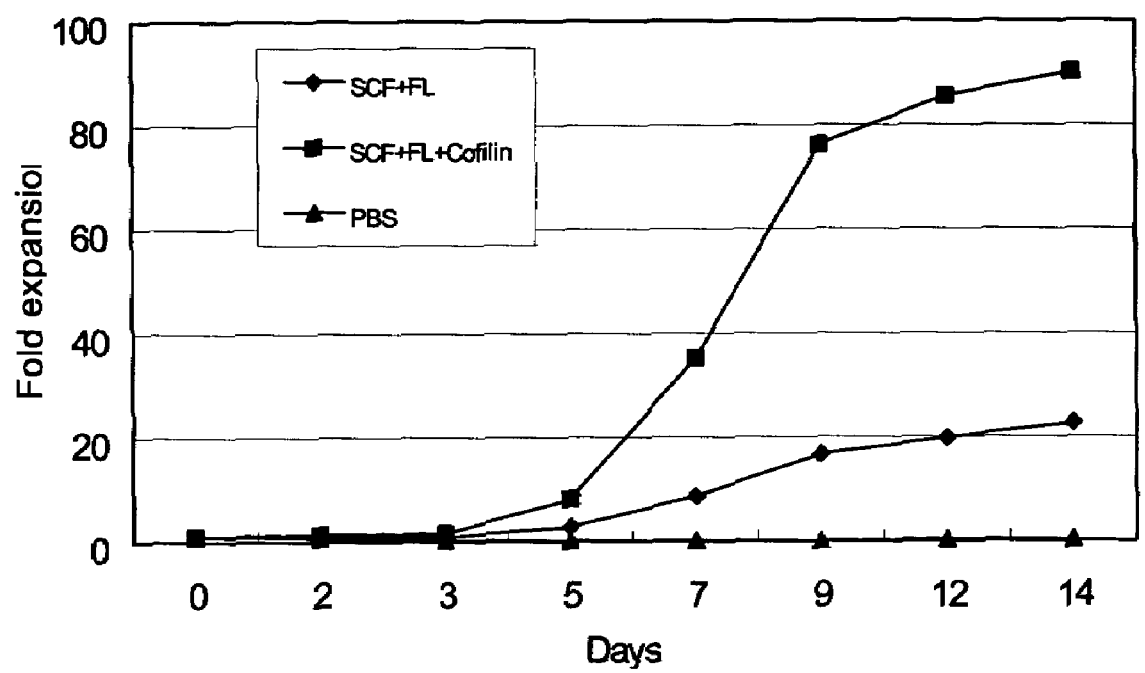
FIG. 5 shows that human nonmuscle-type Cofilin when combined with SCF and FL had a remarkable ability to expand human umbilical cord blood derived CD34 positive cells as compared with the case where only SCF and FL were added.

For the SCF+FL group, human SCF (100 ng/ml, R&D) and human Flt-3 ligand (FMS-like tyrosine kinase 3 Ligand, FL; 100 ng/ml, R&D) were added to the prepared culture plate. For the SCF+FL+Cofilin group, human SCF (100 ng/ml, R&D), human FL (100 ng/ml, R&D) and the recombinant human nonmuscle-type Cofilin containing COS-1 cell's culture supernatant prepared in Example 2 were added, the last having being concentrated 10-fold and a 100-μl portion of the concentrate being added. Thereafter, each group was cultured in a $CO_2$ incubator at 37° C. To the PBS group (control group), neither of the above-mentioned SCF, FL and Cofilin were added but only PBS was added in the same amount. At days 3, 5, 7, 9, 12 and 14 of culture, cell count was taken with a hemocytometer under a microscope. The result was expressed as "Fold Expansion" relative to the initial cell count at the start of culture and is shown in FIG. 5.

As it turned out, the human nonmuscle-type Cofilin in combination with SCF+FL allowed the human umbilical cord blood derived CD34 positive cells to proliferate with time, exhibiting marked growth activity compared to the addition of SCF+FL only. Specifically, at day 14 of culture, the cells had grown to give a count about 90 times higher than the initial cell count (see FIG. 5).

Example 5

Evaluating the Activity of Recombinant Human Nonmuscle-Type Cofilin in Promoting the Growth and/or Differentiation of Human Hematopoietic Stem Cells and/or Hematopoietic Progenitors In order to know whether the recombinant human nonmuscle-type Cofilin had the activity of promoting the growth and/or differentiation of human hematopoietic stem cells and/or hematopoietic progenitors, the inventors made an experiment using the recombinant human nonmuscle-type Cofilin containing culture supernatant of COS-1 cells that was prepared in Example 2, with the ability of various cells to form colonies being adopted as an index of the growth and/or differentiation promoting activity.

First, human umbilical cord blood derived CD34 positive cells were adjusted to a concentration of $2.5 \times 10^4$ cells/ml as noted in Example 4 and then added to a 12-well culture plate in respective amounts of 1 ml/well. The recombinant human nonmuscle-type Cofilin containing COS-1 cell's culture supernatant that was prepared in Example 2 was concentrated 10-fold and a 100-μl portion of the concentrate was added in various combinations with human SCF (100 ng/ml), human FL (100 ng/ml) and/or human TPO (100 ng/ml, R&D); after 7-day culture, the number of cells was counted with a hemocytometer under a microscope. The result was expressed as a multiplication factor relative to the initial cell count at the start of culture and is depicted in FIG. 6A for the following groups: T/C group which was cultured in the presence of human TOP (100 ng/ml, R&D) and the above-mentioned Cofilin containing culture supernatant; S/F/C group cultured in the presence of human SCF (100 ng/ml), human FL (100 ng/ml) and the above-mentioned Cofilin containing culture supernatant; S/F/T group in the presence of human SCF (100 ng/ml), human FL (100 ng/ml) and human TPO (100 ng/ml, R&D); S/F group in the presence of human SCF (100 ng/ml) and human FL (100 ng/ml); C group in the presence of the above-mentioned Cofilin containing culture supernatant; and T group in the presence of human TPO (100 ng/ml, R&D). PBS group refers to culture in the presence of added PBS only.

As it turned out, the human nonmuscle-type Cofilin in combination with SCF and FL (namely, S/F/C group) caused human umbilical cord blood derived CD34 positive cells to expand significantly and showed a growth activity which was about 6 times as high as the activity of the S/F group and about twice the activity of the S/F/T group. At day 7 of the culture, the cell proliferation was about 58 times the Input (the number of CD34 positive cells in 200 μl of the cell suspension before culture) (see FIG. 6A).

Subsequently, a portion (100 μl) of the suspension of human umbilical cord blood derived CD34 positive cells that had been cultured for 7 days in (1) above was collected and subjected to a colony formation assay by the methyl cellulose method.

The colony formation assay by the methyl cellulose method was performed as follows. Based on □ MEM, a semi-solid medium was supplemented with 2.2% methyl cellulose (Shin-Etsu Chemical Co., Ltd.), 30% FCS, 1% BSA, $5 \times 10^{-5}$ M 2ME (Wako Pure Chemical Industries, Ltd.), SCF (100 ng/ml), IL-3 (20 ng/ml), TPO (10 ng/ml, R&D), granulocyte colony stimulating factor (G-CSF; 10 ng/ml, CHUGAI PHARMACEUTICAL CO., LTD.) and erythropoietin (EPO; 2 U/ml, KIRIN BEVERAGE CO., LTD.) and the collected CD34 positive cells were cultured in the resulting medium for 2 weeks at 37° C. in the presence of 5% $CO_2$ so as to form a variety of cell colonies.

Among the various cell colonies formed, colonies of granulocyte/macrophage associated progenitors (colony-forming unit granuloyte, macrophage, CFU-GM), erythroid associated progenitors (burst-forming unit erythroid, BFU-E) and myeloid associated stem cells (colony-forming unit mixed, FU-Mix) were identified and colony counts were taken on the basis of visual observation under an inverted microscope. CFU-GM refers to cell masses consisting of granulocyte masses which were dense aggregates of smaller cells and coarse macrophage masses which were aggregates of larger cells and such cell colonies were distinguished from BFU-E which refers to larger masses of cells that turned red due to hemoglobin synthesis. As for masses that were difficult to distinguish and those which did not take on a typical colony morphology, cytospun samples were prepared and evaluation was made by May-Giemsa staining. Fifty and more cell masses consisting granulocytes and macrophage were evaluated as a CFU-GM colony whereas 500 and more cell masses of erythrocytes were evaluated as a BFU-E colony; a colony comprising BFU-E and at least 50 cells of other lineages was evaluated as a CFU-Mix colony. The results were each expressed as "Fold Expansion" relative to the initial cell count at the start of culture and are depicted in FIGS. 6B to 6D for CFU-GM, BFU-E and CFU-Mix colonies, respectively.

The human nonmuscle-type Cofilin combined with SCF and FL (as in the S/F/C group) allowed the human umbilical cord blood derived CD34 positive cells to expand and the cells were thereafter subjected to a colony formation assay. As it turned out, the CFU-GM, BFU-E and CFU-Mix colony counts were expanded about 4, 6 and 8 times as many as the Input (the number of colonies in 200 µl of the cell suspension before culture), respectively (see FIGS. 6B, 6C and 6D). In particular, the numbers of BFU-E and CFU-Mix colonies were much more greater than any other cytokines combinations.

Example 6

Evaluating the Activity of Recombinant Human nonmuscle-type Cofilin in Promoting the Growth and/or Differentiation of Human Megakaryocytic Progenitors In order to know whether the recombinant human nonmuscle-type Cofilin had the activity of promoting the growth and/or differentiation of human megakaryocytic progenitors, the inventors made an experiment using the recombinant human nonmuscle-type Cofilin containing culture supernatant of COS-1 cells that was prepared in Example 2, with the ability of megakaryocyte progenitors (colony-forming unit megakaryocyte, CFU-Mk) to form colonies being adopted as an index of the growth and/or differentiation promoting activity.

First, human umbilical cord blood derived CD34 positive cells were adjusted to a concentration of $2.5 \times 10^4$ cells/ml as noted in Example 4 and then added to a 12-well culture plate in respective amounts of 1 ml/well. The recombinant human nonmuscle-type Cofilin containing COS-1 cell's culture supernatant that was prepared in Example 2 was concentrated 10-fold and a 100-µl portion of the concentrate, human SCF (100 ng/ml), human FL (100 ng/ml) and human TPO (100 ng/ml, R&D) were added in the combinations described in Example 5, namely, to provide T/C group, S/F/C group, S/F/T group, S/F group, C group and T group, and 7-day culture was effected. PBS group refers to culture in the presence of added PBS only.

Figure 7:
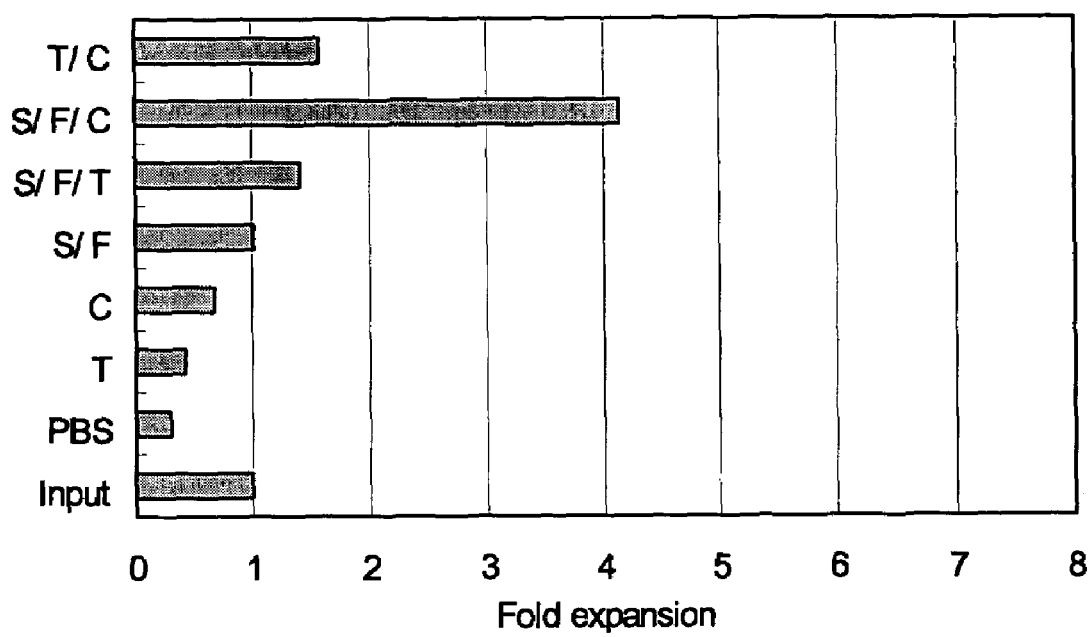
FIG. 7 shows that when human umbilical cord blood derived CD34 positive cells as grown under the condition of human nonmuscle-type Cofilin+SCF+FL were subjected to colony forming assay, a significant increase occurred in the colony number of CFU-Mk.

Subsequently, a portion of the suspension of human umbilical cord blood derived CD34 positive cells that had been cultured for 7 days was collected and cultured using MegaCult-C (Stem Cell Technologies) to form CFU-Mk colonies, followed by identification of the megakaryocytes and counting of the number of their colonies. To be more specific, a portion (100 µl) of the cell suspension was added to a collagen gel (containing IL-3, IL-6 and TPO); the stirred mixture was transferred into culture slide chambers and cultured for 12-14 days to form CFU-Mk colonies. The cells on the slides were fixed with methanol/acetone and megakaryocytes were detected by immunostaining with anti-GP (glycoprotein) IIb/IIIa (marker of human megakaryocytes) and cell nucleus staining with Evans Blue. In Example 6, a cell mass found to consist of 20 or more megakaryocytes by microscopic observation was determined as a CFU-Mk colony. The result was expressed as "Fold Expansion" relative to the initial cell count at the start of culture and is depicted in FIG. 7.

The human nonmuscle-type Cofilin combined with SCF and FL allowed the human umbilical cord blood derived CD34 positive cells to expand and the cells were thereafter subjected to a colony formation assay. As it turned out, the CFU-Mk colonies were expanaded about 4 times as many as the Input (the number of colonies in 200 µl of the cell suspension before culture) (see FIG. 7). The expansion achieved by other cytokines combinations was substantially the same as the Input.

Example 7

Evaluating the Activity of Recombinant Human Nonmuscle-Type Cofilin in Human Megakaryocyte Proplatelet Formation In order to know whether the recombinant human nonmuscle-type Cofilin had the activity of human megakaryocyte proplatelet formation, the inventors made a morphological study using the recombinant human nonmuscle-type Cofilin containing culture supernatant of COS-1 cells prepared in Example 2.

Human umbilical cord blood derived CD34 positive cells were adjusted to a concentration of $5 \times 10^4$ cells/ml on an □ MEM medium supplemented with 1% BSA and GIBCO supplement (insulin, 10 µg/ml; transferrin, 5.5 µg/ml; ethanolamine, 2 mg/ml; selenious acid, 6.7 mg/ml) and were thereafter added to each of the wells on a 12-well culture plate in an amount of 1 ml. Subsequently, the recombinant human nonmuscle-type Cofilin containing COS-1 cell's culture supernatant prepared in Example 2 was concentrated 10-fold and a 100-µl portion of the concentrate and human TPO (100 ng/ml) were added, either individually or in combination, followed by culture at 37° C. in the presence of 5% $CO_2$. At day 7 of the culture, the medium in each well was replenished with 1 ml of a medium of the same composition and culture was continued. Thereafter, observation was made under a microscope to see whether megakaryocyte proplatelets had formed.

Figure 8:
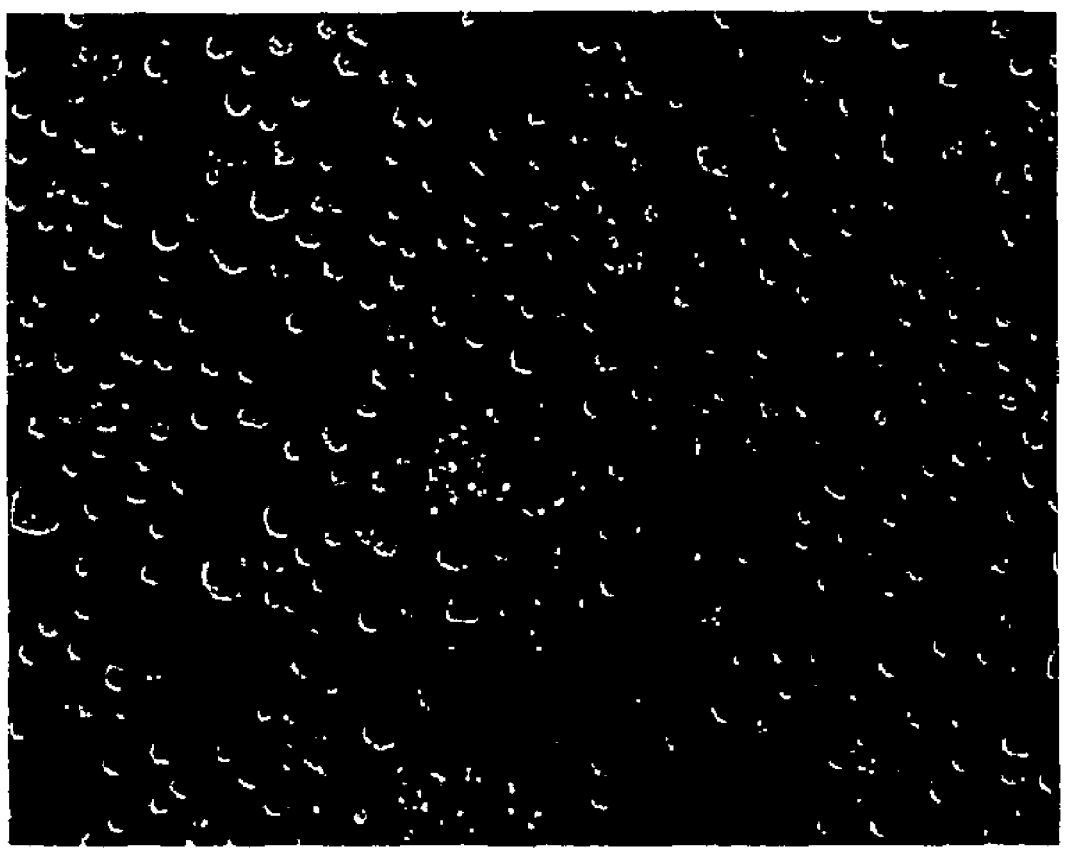
FIG. 8 is a micrograph showing that human nonmuscle-type Cofilin as combined with SCF and FL caused human umbilical cord blood derived CD34 positive cells to differentiate and grow into megakaryocytes.
Figure 9:
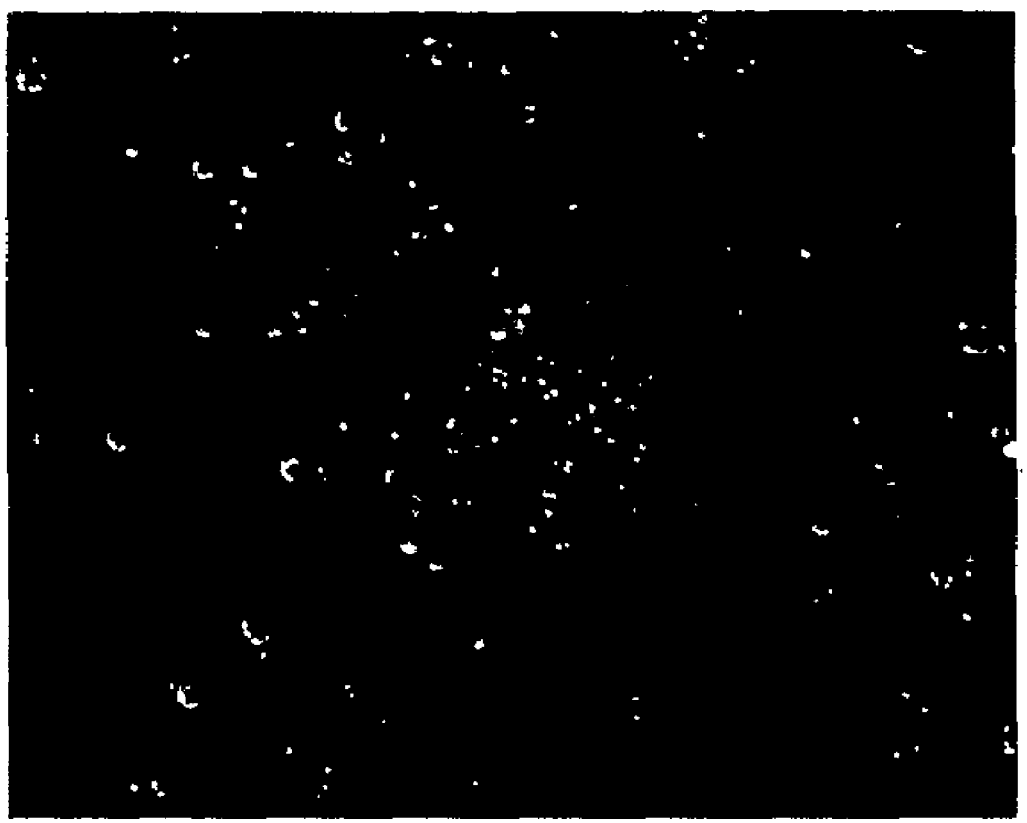
FIG. 9 is a micrograph showing that when human umbilical cord blood derived CD34 positive cells were cultured for about 2 weeks in the presence of human nonmuscle-type Cofilin in combination with SCF and FL, some of the megakaryocytes were found to form proplatelets.

The human nonmuscle-type Cofilin combined with TPO allowed the human umbilical cord blood derived CD34 positive cells to differentiate and grow into megakaryocytes so markedly (FIG. 8) that around 2 weeks of culture, some of the mature megakaryocytes formed visible proplatelets which were believed to reflect the preliminary stage of platelet release (FIG. 9). However, no proplatelet formation was visible when the human nonmuscle-type Cofilin or TPO was added singly.

The invention claimed is:

1. A method of expanding hematopoietic stem cells and/or hematopoietic progenitors in vitro or ex vivo comprising administering Cofilin comprising the amino acid sequence of SEQ ID NO: 1 to hematopoietic stem cells and/or hematopoietic progenitors, and expanding said hematopoietic stem cells and/or hematopoietic progenitors in vitro or ex vivo.

2. A method of treating a disease that results from insufficient growth of hematopoietic stem cells and/or hematopoietic progenitors in a subject, comprising expanding hematopoietic stem cells and/or hematopoietic progenitors ex vivo by administering Cofilin comprising the amino acid sequence of SEQ ID NO: 1 to hematopoietic stem cells and/or hematopoietic progenitors, and transplanting said expanded hematopoietic stem cells and/or hematopoietic progenitors into said subject.

3. The method of claim 1 or 2, wherein the Cofilin is produced by a gene recombinant technique.

4. The method of claim 1 or 2, wherein the Cofilin includes a sugar chain.

5. The method of claim 1 or 2, wherein said method further comprises administering a cytokine.

6. The method of claim 5, wherein said cytokine is interleukin (IL)-1, IL-2, IL-3, IL-4, IL-5, IL-6, IL-7, IL-10 and IL-11, granulocyte colony stimulating factor (G-CSF), granulocyte/macrophage colony stimulating factor (GM-CSF), macrophage colony stimulating factor (M-CSF), erythropoietin (EPO), basic fibroblast growth factor (bFGF), acidic fibroblast growth factor (aFGF), insulin-like growth factor (IGF), epidermal growth factor (EGF), hepatocyte growth factor (HGF), transforming growth factor-α (TGF-α), protease nexin I, protease nexin II, platelet derived growth factor (PDGF), cholinergic differentiation factor (CDF), leukocyte migration inhibitory factor (LIF), stem cell factor (SCF), flk-2flt-3 ligand (FL), thrombopoietin (TPO), IL-6/soluble IL-6 receptor complex, Hyper IL-6 (fusion protein from IL-6 or soluble IL-6 receptor), or any combinations thereof.

7. The method of claim 5, wherein said cytokine is IL-3.

8. The method of claim 5, wherein said cytokine comprises stem cell factor (SCF), flk-2/flt-3 ligand (FL), or a combination thereof.

9. The method of claim 1 or 2, wherein the Cofilin is encoded by SEQ ID NO: 2.

10. The method of claim 2, wherein said disease is panhematopenia or a disease accompanied by hematopoietic hypofunction.

11. A method of promoting differentiation of hematopoietic stem cells and/or hematopoietic progenitors in vitro or ex vivo, said method comprising administering Cofilin comprising the amino acid sequence of SEQ ID NO: 1 and a cytokine to hematopoietic stem cells and/or hematopoietic progenitors, and promoting differentiation of hematopoietic stem cells and/or hematopoietic progenitors in vitro or ex vivo.

12. A method of treating a disease that results from insufficient growth of hematopoietic stem cells and/or hematopoietic progenitors in a subject, comprising expanding hematopoietic stem cells and/or hematopoietic progenitors ex vivo by administering Cofilin comprising the amino acid sequence of SEQ ID NO: 1 and a cytokine to hematopoietic stems cells and/or hematopoietic progenitors, and transplanting said expanded hematopoietic stem cells and/or hematopoietic progenitors into said subject.

13. The method of claim 12, wherein said disease is panhematopenia or a disease accompanied by hematopoietic hypofunction.

14. The method of claim 11 or 12, wherein the Cofilin is produced by a gene recombinant technique.

15. The method of claim 11 or 12, wherein the Cofilin includes a sugar chain.

16. The method of claim 11 or 12, wherein said cytokine is interleukin (IL)-1, IL-2, IL-3, IL-4, IL-5, IL-6, IL-7,IL-10 and IL-11, granulocyte colony stimulating factor (G-CSF), granulocyte/macrophage colony stimulating factor (GM-CSF), macrophage colony stimulating factor (M-CSF), erythropoietin (EPO), basic fibroblast growth factor (bFGF), acidic fibroblast growth factor (aFGF), insulin-like growth factor (IGF), epidermal growth factor (EGF), hepatocyte growth factor (HGF), transforming growth factor-α (TGF-α), protease nexin I, protease nexin II, platelet derived growth factor (PDGF), cholinergic differentiation factor (CDF), leukocyte migration inhibitory factor (LIF), stem cell factor (SCF), flk-2/flt-3 ligand (FL), thrombopoietin (TPO), IL-6/soluble IL-6 receptor complex, Hyper IL-6 (fusion protein from IL-6 or soluble IL-6 receptor), or any combinations thereof.

17. The method of claim 11 or 12, wherein said cytokine is IL-3.

18. The method of claim 11 or 12, wherein said cytokine comprises stem cell factor (SCF), flk-2/flt-3 ligand (FL), or a combination thereof.

19. The method of claim 11 or 12, wherein the Cofilin is encoded by SEQ ID NO: 2.

\* \* \* \* \*